(12) United States Patent
Bosques et al.

(10) Patent No.: US 9,103,821 B2
(45) Date of Patent: Aug. 11, 2015

(54) METHODS RELATED TO MODIFIED GLYCANS

(75) Inventors: Carlos J. Bosques, Arlington, MA (US); Jennifer Lynn Murphy, Marshfield, MA (US); Sibel Nur Gunay, Chestnut Hill, MA (US); Zachary Shriver, Winchester, MA (US); Cuihua Liu, Belmont, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 229 days.

(21) Appl. No.: 13/140,553

(22) PCT Filed: Dec. 18, 2009

(86) PCT No.: PCT/US2009/068790
§ 371 (c)(1),
(2), (4) Date: Aug. 29, 2011

(87) PCT Pub. No.: WO2010/071824
PCT Pub. Date: Jun. 24, 2010

(65) Prior Publication Data
US 2011/0306075 A1 Dec. 15, 2011

Related U.S. Application Data

(60) Provisional application No. 61/139,224, filed on Dec. 19, 2008.

(51) Int. Cl.
*G01N 33/50* (2006.01)
*G01N 33/52* (2006.01)
*C12Q 1/34* (2006.01)
*G01N 33/53* (2006.01)

(52) U.S. Cl.
CPC .............. *G01N 33/5308* (2013.01); *C12Q 1/34* (2013.01); *G01N 33/50* (2013.01); *G01N 33/52* (2013.01); *G01N 2400/38* (2013.01)

(58) Field of Classification Search
None
See application file for complete search history.

(56) References Cited

U.S. PATENT DOCUMENTS

| | | | |
|---|---|---|---|
| 5,122,469 A | 6/1992 | Mather et al. | |
| 5,633,162 A | 5/1997 | Keen et al. | |
| 6,045,854 A * | 4/2000 | Prieto et al. | 426/658 |
| 6,096,555 A | 8/2000 | Hermentin et al. | |
| 2006/0127950 A1 * | 6/2006 | Bosques et al. | 435/7.1 |
| 2006/0270048 A1 * | 11/2006 | Dwek et al. | 436/67 |
| 2007/0178551 A1 | 8/2007 | Gerngross | |
| 2008/0044383 A1 | 2/2008 | Sackstein | |
| 2009/0148839 A1 * | 6/2009 | Laine et al. | 435/6 |

FOREIGN PATENT DOCUMENTS

| | | |
|---|---|---|
| WO | WO/2007/047687 | 4/2007 |
| WO | WO/2007/061936 | 5/2007 |
| WO | WO-2008/128228 A1 | 10/2008 |
| WO | WO/2008/130926 | 10/2008 |

OTHER PUBLICATIONS

Balaguer, E. et al "Glycoform characterization of erythropoietin . . . " Electrophoresis (2006) vol. 27, pp. 2638-2650.*
Skibeli, V. et al "Sugar profiling proves that human serum erythropoietin differs . . . " Hematopoiesis (2001) vol. 98, No. 13, pp. 3626-3634.*
Stehling, P. et al "Rapid analysis of O-acetylated neuraminic acids . . . " Glycoconj. J. (1998) vol. 15, pp. 339-344.*
Yagi, H. et al., Development of structural analysis of sulfated N-glycans by multidimensional high performance liquid chromatography mapping methods, Glycobiology, 15(10):1051-1060 (2005).
Gil, G. C. et al., "A relative and absolute quantification of neutral N-linked oligosaccharides using modification with carboxymethyl trimethylammonium hydrazide and matrix-assisted laser desorption/ionization time-of-flight mass spectrometry," Analytical Biochemistry, Academic Press Inc., New York, vol. 379, No. 1, Apr. 27, 2008.
Hamid, U. M. Abd et al., "A strategy to reveal potential glycan markers from serum glycoproteins associated with breast cancer progression," Glycobiology, vol. 18, No. 12, Sep. 25, 2008.
Supplementary European Search Report, EP 09833844.5 filed on Dec. 18, 2009, published as EP 2358731 on Aug. 24, 2011, mailed on Jun. 28, 2012.
Anumula, KR, "Advances in fluorescence derivatization methods for high-performance liquid chromatographic analysis of glycoprotein carbohydrates," Anal. Biochem. 350(1): 1-23, 2006.
Fryer and Lannan, "Three decades of fish cell culture: a current listing of cell lines derived from fishes," *J. Tissue Culture Methods*, 16: 87-94, 2005.
Hara, et al., *Anal. Biochem.*, 179: 162-166, 1989.
Huang, Y., et al., "Microscale nonreductive release of O-linked glycans for subsequent analysis through MALDI mass spectrometry and capillary electrophoresis," *Anal. Chem.* 73(24): 6063-6069, 2001.
International Search Report for PCT/US09/068790 mailed Sep. 2, 2010.
O'Neill, R.A., "Enzymatic release of oligosaccharides from glycoproteins for chromatographic and electrophoretic analysis," *J. Chromotogr. A.*, 720(1-2): 201-215, 1996.
Prime, S., et al., "Oligosaccharide sequencing based on exo- and endo-glycosidase digestion and liquid chromatographic analysis of the products," *J. Chromatogr. A.*, 720(1-2): 263-274, 1996.
Written Opinion for PCT/US09/068790 mailed Sep. 2, 2010.
Yuan, et al., "Isotope tag method for quantitative analysis of carbohydrates by liquid chromatography-mass spectrometry," *J. Chromotography A*, 1067(1-2): 145-152, 2005.

* cited by examiner

*Primary Examiner* — Leigh Maier
(74) *Attorney, Agent, or Firm* — Choate Hall & Stewart LLP; Brenda Herschbach Jarrell; Rolando Medina

(57) ABSTRACT

Among other things, the present disclosure provides methods for enriching, identifying, and/or quantifying unusually modified glycans (e.g., phosphorylated glycans, sulfated glycans, and/or multi-acetylated glycans). In many embodiments, methods comprise providing a glycan preparation from which sialic acids have been released; subjecting the sialidase-treated glycan preparation to a separation technique that separates glycans based on charge-to-mass ratio; and quantifying the charged products using at least one quantification standard.

33 Claims, 7 Drawing Sheets

Mannose-6-phosphate (M6P)
(6-Sulfo-GlcNAc)

6-Sulfo-N-Acetylglucosamine

N-Acetylneuraminic Acid
(Neu5Ac)

US 9,103,821 B2

METHODS RELATED TO MODIFIED GLYCANS

The present application claims priority to U.S. Provisional patent application Ser. No. 61/139,224, filed on Dec. 19, 2008, the entire disclosure of which is incorporated herein by reference.

BACKGROUND

Modifications to glycans on a glycoconjugate (e.g., glycoprotein) often significantly impact the function of the glycoconjugate. For example, glycan modifications can affect a glycoprotein's ability to fold correctly, stability (e.g. resistance to proteolytic and/or other degradation), catalytic activity, pharmacodynamic and/or pharmacokinetic properties, and/or interaction with other molecules. A glycoprotein's glycan modifications can affect transport and targeting of the glycoprotein. For example, a glycoprotein's glycan modifications can affect whether the glycoprotein remains intracellular (including, e.g., correct targeting of the glycoprotein to the proper subcellular compartment or compartments), whether the glycoprotein will be membrane-bound, and/or whether the glycoprotein will be secreted from the cell.

SUMMARY

Glycans are commonly modified by sialylation, that is, by addition of a sialic acid. Unusual modifications to glycans such as sulfation, phosphorylation, and multi-acetylated sialylation (e.g., diacetylated sialylation) are often overlooked when analyzing glycoproteins. Such modifications may be overlooked at least in part due to complexities of their analysis and the instability of such modifications. The present disclosure encompasses the recognition that unusual modifications are nonetheless biologically relevant and that methods to identify and quantify them are desirable.

Among other things, the present disclosure provides methods for enriching, identifying, detecting, and/or quantifying unusually modified glycans. In many embodiments, methods comprise providing a glycan preparation from which sialic acids have been released (e.g., a sialidase-treated glycan preparation). This preparation includes glycans (i.e., sialidase-resistant glycans) that were not cleaved by the treatment releasing sialic acids. Provided methods typically include subjecting the provided glycan preparation to a separation technique that separates glycans having a first charge from uncharged glycans and/or glycans having a second charge, and/or that separates glycans based on their charge-to-mass ratio; and optionally quantifying separated glycans. In many embodiments, quantifying comprises using at least one quantification standard.

DEFINITIONS

Figure 1:
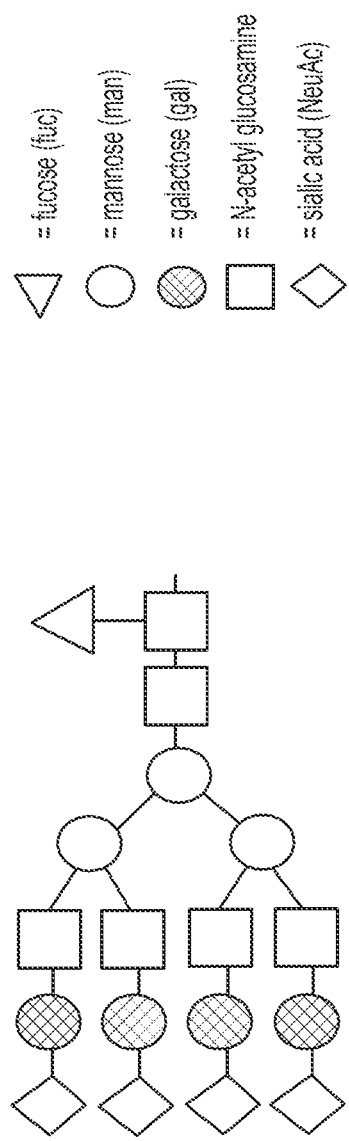
FIG. 1 depicts a structure of an exemplary N-linked glycan.

Acetyl: As used herein, the term "acetyl" (also known as "ethanoyl" and often abbreviated as "Ac") is used herein to refer to a functional group with the chemical formula —COCH$_3$.

Acetylated: As used herein, the term "acetylated" means modified by covalent addition of an acetyl group. For example, an acetylated glycan is a glycan that is modified by covalent addition of one or more acetyl groups. An acetylated glycan may or may not have additional modifications.

Acetylation: As used herein, the term "acetylation" (also known in IUPAC nomenclature as "ethanoylation") refers to the process of covalently adding one or more acetyl groups to a molecule (e.g., to a glycan).

Approximately, About, Ca.: As used herein, the terms "approximately", "about" or "ca.," as applied to one or more values of interest, refer to a value that is similar to a stated reference value. In certain embodiments, the terms "approximately," "about," or "ca." refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1% or less of the stated reference value.

Biological sample: The term "biological sample", as used herein, refers to any solid or fluid sample obtained from, excreted by or secreted by any living cell or organism, including, but not limited to, tissue culture, bioreactor sample, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

Cell-surface glycoprotein: As used herein, the term "cell-surface glycoprotein" refers to a glycoprotein, at least a portion of which is present on the exterior surface of a cell. In some embodiments, a cell-surface glycoprotein is a protein that is positioned on the cell surface such that at least one of the glycan structures is present on the exterior surface of the cell.

Cell-surface glycan: A "cell-surface glycan" is a glycan that is present on the exterior surface of a cell. In many embodiments of the present disclosure, a cell-surface glycan is covalently linked to a polypeptide as part of a cell-surface glycoprotein. A cell-surface glycan can also be linked to a cell membrane lipid.

Correlating: The term "correlating", as used herein, refers to the establishment of a predictable relationship between two things. In embodiments described herein, a glycosylation pattern (or a characteristic thereof) on the surface of a cell is correlated with a glycosylation pattern (or a characteristic thereof) of a target glycoconjugate (e.g., glycoprotein) produced by the cell. The correlated patterns (or characteristics) need not be identical with one another so long as one can be predicted from the other. Once a correlation is established, it can be recorded, for example, in a written record or can otherwise be affixed in a medium or memory source (e.g., a computer-readable medium or computer memory bank or disc). Detection of a correlated glycosylation pattern (or characteristic thereof) can then involve reference to the written or affixed record, or to a comparator experiment confirming the correlation, etc. Such a comparator experiment may be performed simultaneously with an assessment of glycosylation pattern (or characteristic thereof), or can be a historical or future experiment.

Figure 2:
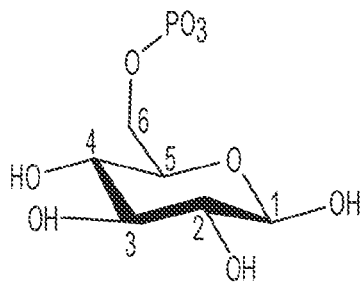
FIG. 2 depicts non-limiting examples of modified residues in glycans: mannose-6-phosphate (M6P) and 6-sulfo-N-Acetylglucosamine (6-sulfo-GlcNAc). The structure of a common sialic acid, N-Acetylneuraminic Acid (Neu5Ac) is depicted without additional modifications for clarity. Acetylation is normally present at the 5 position (shown); additional acetylation may occur at positions 7, 8, and 9. As used herein, "multi-acetylated" in reference to a sialic acid refers to additional acetylation at two or more of the 7, 8, and 9 positions. "Diacetylated" is used in reference to sialic acid to refer to additional acetylation at two of the 7, 8, and 9 positions.
Figure 2:
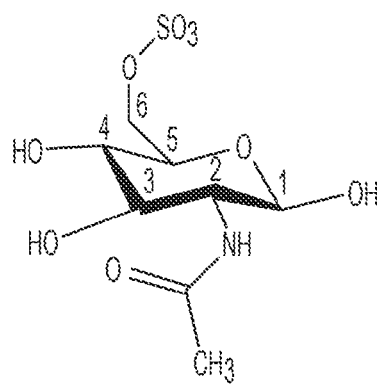
Figure 2:
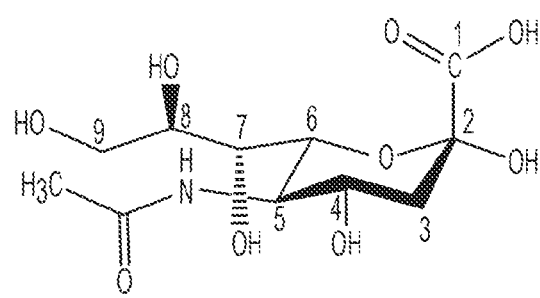

Diacetylation: As used herein, the term "diacetylation" refers to acetylation at two positions on a molecule where acetylation is not usually found. When used in reference to modifications of sialic acid molecules, "diacetylation" refers to acetylation at two positions in addition to acetylation at position 5, which is typically acetylated in sialic acids. In some embodiments, diacetylation of sialic acid molecules comprises acetylation of two of the 7, 8, and 9 positions. (See FIG. 2.)

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

Glycan preparation: The term "glycan preparation" as used herein refers to a set of glycans obtained according to a particular production method. In some embodiments, "glycan preparation" refers to a set of glycans obtained from a glycoprotein preparation (see definition of glycoprotein preparation below). In certain embodiments, glycan preparations comprise sialidase-resistant glycans.

Glycoconjugate: The term "glycoconjugate", as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, glycolipids, proteoglycans, etc.

Glycoform: The term "glycoform", is used herein to refer to a particular form of a glycoconjugate. That is, when the same backbone moiety (e.g., polypeptide, lipid, etc) that is part of a glycoconjugate has the potential to be linked to different glycans or sets of glycans, then each different version of the glycoconjugate (i.e., where the backbone is linked to a particular set of glycans) is referred to as a "glycoform".

Glycolipid: The term "glycolipid" as used herein refers to a lipid that contains one or more covalently linked sugar moieties (i.e., glycans). The sugar moiety(ies) may be in the form of monosaccharides, disaccharides, oligosaccharides, and/or polysaccharides. The sugar moiety(ies) may comprise a single unbranched chain of sugar residues or may be comprised of one or more branched chains. In certain embodiments, sugar moieties may include sulfate and/or phosphate groups. In certain embodiments, glycoproteins contain O-linked sugar moieties; in certain embodiments, glycoproteins contain N-linked sugar moieties.

Glycoprotein: As used herein, the term "glycoprotein" refers to a protein that contains a peptide backbone covalently linked to one or more sugar moieties (i.e., glycans). As is understood by those skilled in the art, the peptide backbone typically comprises a linear chain of amino acid residues. In certain embodiments, the peptide backbone spans the cell membrane, such that it comprises a transmembrane portion and an extracellular portion. In certain embodiments, a peptide backbone of a glycoprotein that spans the cell membrane comprises an intracellular portion, a transmembrane portion, and an extracellular portion. In certain embodiments, methods of the present disclosure comprise cleaving a cell surface glycoprotein with a protease to release the extracellular portion of the glycoprotein, or a portion thereof, wherein such exposure does not substantially rupture the cell membrane. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. Alternatively or additionally, sugar moieties may be modified by diacetylation. In certain embodiments, glycoproteins contain O-linked sugar moieties; in certain embodiments, glycoproteins contain N-linked sugar moieties. In certain embodiments, methods disclosed herein comprise a step of analyzing any or all of cell surface glycoproteins, liberated fragments (e.g., glycopeptides) of cell surface glycoproteins, cell surface glycans attached to cell surface glycoproteins, peptide backbones of cell surface glycoproteins, fragments of such glycoproteins, glycans and/or peptide backbones, and combinations thereof.

Glycoprotein preparation: A "glycoprotein preparation", as that term is used herein, refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms. In some embodiments, the present invention provides methods and reagents for analyzing different preparations of the same glycoprotein (i.e., having identical amino acid sequence). In some embodiments, the present invention provides methods and reagents for analyzing preparations of two (or more) glycoproteins whose amino acid sequences show at least 85%, 90%, 91%, 92%, 93%, 94%, 95%, 96%, 97%, 98%, 99% identity, or greater.

Glycosidase: The term "glycosidase" as used herein refers to an agent that cleaves a covalent bond between sequential sugars in a glycan or between the sugar and the backbone moiety (e.g., between sugar and peptide backbone of glycoprotein). In some embodiments, a glycosidase is an enzyme. In certain embodiments, a glycosidase is a protein (e.g., a protein enzyme) comprising one or more polypeptide chains. In certain embodiments, a glycosidase is a chemical cleavage agent.

Glycosylation pattern: As used herein, the term "glycosylation pattern" refers to the set of glycan structures present on a particular sample. For example, a particular glycoconjugate (e.g., glycoprotein) or set of glycoconjugates (e.g., set of glycoproteins) will have a glycosylation pattern. In some embodiments, reference is made to the glycosylation pattern of cell surface glycans, or a "surface glycosylation pattern." As used herein, a "surface glycosylation pattern" may refer to the pattern of glycans (or "glycosylation pattern") that exists on the extracellular domain of a single cell surface glycoprotein and/or glycolipid of interest. Additionally or alternatively, a "surface glycosylation pattern" may refer to the pattern of glycans ("or glycosylation pattern") that exists on the extracellular domain of a plurality of cell surface glycoproteins and/or glycolipids. In certain embodiments, a "surface glycosylation pattern" describes the pattern of glycans (or "glycosylation pattern") that exists on the entire complement of cell surface glycoproteins and/or glycolipids. Based on context, those of ordinary skill in the art will readily understand whether "surface glycosylation pattern" refers to the glycosylation pattern of a plurality of cell surface glycoproteins and/or glycolipids. A glycosylation pattern can be characterized by, for example, the identities of glycans, amounts (absolute or relative) of individual glycans or glycans of particular types, degree of occupancy of glycosylation sites, modifications of glycans (e.g., sialylation, multi-acetylated sialylation, phosphorylation, sulfation, etc.), etc., or combinations of such parameters.

Multi-acetylation: As used herein, the term "multi-acetylation" refers to acetylation at two or more positions on a molecule where acetylation is not usually found. When used in reference to modifications of sialic acid molecules, "multi-acetylation" refers to acetylation at two or more positions in addition to acetylation at position 5, which is typically acetylated in sialic acids. In some embodiments, multi-acetylation of sialic acid molecules comprises acetylation of two or more of the 7, 8, and 9 positions. (See FIG. 2.)

N-glycan: The term "N-glycan," as used herein, refers to a polymer of sugars that has been released from a glycoconjugate but was formerly linked to the glycoconjugate via a nitrogen linkage (see definition of N-linked glycan below).

N-linked glycan: The term "N-linked glycan," as used herein, refers to a glycan that is linked to a glycoconjugate via a nitrogen linkage. A diverse assortment of N-linked glycans exists, but is typically based on the common core pentasaccharide $(Man)_3(GlcNAc)(GlcNAc)$.

O-glycan: The term "O-glycan," as used herein, refers to a polymer of sugars that has been released from a glycoconjugate but was formerly linked to the glycoconjugate via an oxygen linkage (see definition of O-linked glycan below).

O-linked glycan: The term "O-linked glycans," as used herein, refers to a glycan that is linked to a glycoconjugate via an oxygen linkage. O-linked glycans are typically attached to glycoproteins via N-acetyl-D-galactosamine (GalNAc) or via N-acetyl-D-glucosamine (GlcNAc) to the hydroxyl group of L-serine (Ser) or L-threonine (Thr). Some O-linked glycans also have modifications such as acetylation and sulfation. In some instances O-linked glycans are attached to glycoproteins via fucose or mannose to the hydroxyl group of L-serine (Ser) or L-threonine (Thr).

Phosphate: As used herein, the term "phosphate" is used herein to refer to a $PO_4^-$ group (in free solution), or an $PO_3$ group (as part of a compound). As part of a chemical name, the term "phosphate" refers to the chemical modified by the addition of a phosphate group.

Phosphorylated: As used herein, the term "phosphorylated" means modified by covalent addition of a phosphate group. For example, a phosphorylated glycan is a glycan that is modified by covalent addition of one or more phosphorylated groups. A phosphorylated glycan may or may not have additional modifications.

Phosphorylation: As used herein, the term "phosphorylation" refers to the process of covalently adding one or more phosphate groups to a molecule (e.g., to a glycan).

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Protein: In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

Sialic acid: The term "sialic acid," as used herein, is a generic term for the N- or O-substituted derivatives of neuraminic acid, a nine-carbon monosaccharide. The amino group of neuraminic acid typically bears either an acetyl or a glycolyl group in a sialic acid. The hydroxyl substituents present on the sialic acid may be modified by acetylation, methylation, sulfation, and phosphorylation. The predominant sialic acid is N-acetylneuraminic acid (Neu5Ac). Sialic acids impart a negative charge to glycans, because the carboxyl group tends to dissociate a proton at physiological pH. Exemplary deprotonated sialic acids are as follows:

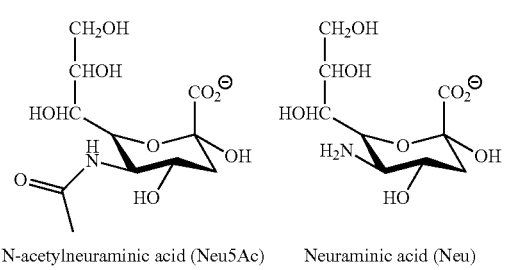

N-acetylneuraminic acid (Neu5Ac)    Neuraminic acid (Neu)

Sialidase: As used herein, the term "sialidase" (also spelled "sialydase") refers to an agent that cleaves sialic acid residues from glycans. In some embodiments, a sialidase is an enzyme. In certain embodiments, a sialidase is a protein (e.g., a protein enzyme) comprising one or more polypeptide chains. In certain embodiments, a sialidase is a chemical cleavage agent; in some such embodiments, a sialidase is a mild acid.

Sialidase-resistant: As used herein, the term "sialidase-resistant," when used to refer to glycans, describes the characteristic of being substantially resistant to cleavage by sialidase treatment as defined herein. For example, glycans that are sialidase-resistant may lack sialidase modifications. Additionally or alternatively, sialidase-resistant glycans may comprise modifications that cannot be substantially cleaved by sialidase treatment. Examples of such modifications include sulfation, phosphorylation, and/or multi-acetylated sialylation. As used herein, "sialidase-resistant" glycans encompass glycans that contain both sialic acid modifications and other modifications that cannot be substantially cleaved by sialidase treatment. For example, a glycan molecule with both sialic acid modifications and phosphorylation is sialidase-resistant.

Sialidase treatment: As used herein, "sialidase treatment" refers to treatment with an agent under appropriate conditions as to allow cleavage of a substantial proportion of linkages of sialic acid residues. In some embodiments, sialidase treatment results in release of sialic acids from molecules such as glycans. In some embodiments, the agent is an enzyme polypeptide such as a sialidase polypeptide. In some embodiments, the agent is a chemical agent such as a mild acid or a combination of mild acids. In some embodiments, a combination of agents that have sialidase activity is used in a sialidase treatment. Accordingly, a "sialidase-treated" sample such as, for example, a sialidase-treated glycan preparation, has undergone treatment with an agent under such conditions as to allow cleavage of a substantial proportion of linkages of sialic acid residues.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. To give but one particular example, when it is said that a treatment does not "substantially" rupture the cell membranes, it is meant to indicate that all or most of the cell membranes remain intact during and after the treatment, for example so that intracellular glycoproteins or glycopeptides are thus not released from the cells. In certain embodiments, the term "substantially", as applied to unruptured cell membranes, refers to condition wherein 15%, 10%, 9%, 8%, 7%, 6%, 5%, 4%, 3%, 2%, 1%, or fewer of the cells subjected to a particular treatment exhibit measurable ruptured cell membranes. In certain embodiments, the term "substantially", as applied to unruptured cell membranes, refers to condition wherein none of the cells subjected to a particular treatment exhibit measurable ruptured cell membranes.

Sulfate: As used herein, the term "sulfate" is used herein to refer to an $SO_4^-$ group (in free solution), or an $SO_3$ group (as part of a compound), and is alternatively spelled "sulphate." As part of a chemical name, the term "sulfate" refers to the chemical modified by the addition of a sulfate group.

Sulfated: As used herein, the term "sulfated" means modified by covalent addition of a sulfate group, and is alternatively spelled "sulphated." For example, a sulfated glycan is a glycan that is modified by covalent addition of one or more sulfate groups. A sulfated glycan may or may not have additional modifications.

Sulfation: As used herein, the term "sulfation" refers to the process of covalently adding one or more sulfate groups to a molecule (e.g., to a glycan).

Unusual modifications: As used herein, the term "unusual modifications," when used in reference to modifications to glycans, refer to modifications other than sialylation without modifications to the sialic acids, other than acetylation at the 5 position. Non-limiting examples of unusual modifications include phosphorylation, sulfation, and multi-acetylated sialylation. For example, mannose residues can be phosphorylated at the C-6 position, N-acetylglucosamine resides can be sulfated at the C-6 position, sialic acid residues can be acetylated at two of the 7, 8, and 9 positions in addition to being acetylated at the usual 5 position, etc.

DETAILED DESCRIPTION OF CERTAIN PREFERRED EMBODIMENTS

As described herein, the present disclosure relates to methods of enriching, identifying, detecting, and/or quantifying unusually modified glycans in a mixture. Generally, unusually modified glycans comprise modifications other than sialylation that impart a charge onto the glycans. In some embodiments, the charge is a negative charge. Examples of unusual modifications include phosphorylation, sulfation, multi-acetylated sialylation, or a combination thereof. In many embodiments, methods comprise providing a glycan preparation from which sialic acids have been released; subjecting the glycan preparation to a separation technique that separates glycans based on charge to mass ratio; and quantifying at least one separated glycan. In many embodiments, such quantifying involves using at least one quantification standard.

I. Glycan Preparations from which Sialic Acids have been Released

In general, glycan preparations are provided by obtaining material from a source of glycans and treating the material. The term "glycan preparation" as used herein typically refers to material comprising glycans after the material has undergone treatment to release glycans. In many embodiments, glycan preparations also undergo a treatment and/or process to release sialic acids from the preparation. In some embodiments, the treatment to release sialic acids comprises sialidase treatment as described herein. Glycan preparations that have also undergone sialidase treatment are herein termed "sialidase-treated glycan preparations." The term "sialidase-treated glycan preparation," as used herein encompasses material that has undergone processing in addition to the described treatment.

Glycans can be obtained from a variety of sources as discussed below. In order to facilitate a better understanding of provided methods, a description of glycans and glycoconjugates is provided A. Glycans and Glycoconjugates In general, a glycan refers to a carbohydrate moiety which, in some embodiments, is covalently attached to a glycoprotein. Carbohydrate moieties (e.g., oligosaccharide chains) are linked to glycoproteins in the endoplasmic reticulum and in the Golgi apparatus via either N-linkages or O-linkages. The present disclosure encompasses the recognition that it is beneficial to determine unusual modifications (such as phosphorylation) of glycans (e.g., glycans that are conjugated to polypeptides in glycoproteins). Methods described herein may be used to analyze unusual modifications (e.g., amount within a glycan preparation, chemical nature of modification, etc.) of any glycan. Methods may alternatively or additionally be used to enrich for unusually modified glycan species.

1. N-Linked Glycans

Typically, N-linked oligosaccharide chains are added to glycoproteins in the lumen of the endoplasmic reticulum (see Alberts et al., Molecular Biology of the Cell, 1994, incorporated herein by reference). Carbohydrate moieties are added to the amino group on the side chain of an asparagine residue contained within the target consensus sequence of Asn-X-Ser/Thr, where X may be any amino acid except proline. The initial oligosaccharide chain is usually trimmed by specific glycosidase enzymes in the endoplasmic reticulum, resulting in a short, branched core oligosaccharide composed of two N-acetylglucosamine and three mannose residues.

N-linked glycans and N-glycans can be subdivided into three distinct groups called "high mannose type," "hybrid type," and "complex type," with a common pentasaccharide core (Manp($\alpha$1,6)-(Manp($\alpha$1,3))-Manp($\beta$1,4)-GlcNAc($\beta$1,4)-GlcNAc($\beta$1,N)-Asn) occurring in all three groups. Modifications to the core include, for example, additional glycosylation, providing a bisecting GlcNAc, attachment of a fucosyl residue on the innermost GlcNAc, and capping with sialic acid (Neu) residues. An exemplary N-linked glycan structure is depicted in FIG. 1. As shown in FIG. 1, structural variation of N-linked glycans mostly occurs with respect to the (up to) 4 antennae at the left hand side of the N-linked glycans depicted in FIG. 1. N-linked glycans are commonly found as components of peptides (i.e., a glycopeptide) and proteins (i.e., a glycoprotein).

After initial processing in the endoplasmic reticulum, glycoproteins are then transported to the Golgi where further processing may take place. Trimmed N-linked oligosaccharide chains may be modified by addition of several mannose residues, resulting in a "high-mannose oligosaccharide." Alternatively or additionally, one or more monosaccharide units of N-acetylglucosamine may be added to the core mannose subunits to form "complex oligosaccharides." Galactose may be added to N-acetylglucosamine subunits, and sialic acid subunits may be added to galactose subunits, resulting in chains that terminate with any of a sialic acid, a galactose, or an N-acetylglucosamine residue. A fucose residue may be added to an N-acetylglucosamine residue of the core oligosaccharide. Each of these additions is catalyzed by specific glycosyl transferases.

'Hybrid glycans' comprise characteristics of both high-mannose and complex glycans. For example, one branch of a hybrid glycan may comprise primarily or exclusively mannose residues, while another branch may comprise N-acetylglucosamine, sialic acid, galactose, and/or fucose sugars.

N-linked glycans are involved in a variety of cellular processes. For example, N-linked glycans contribute to proper protein folding in eukaryotic cells. Chaperone proteins in the endoplasmic reticulum (e.g., calnexin and calreticulin) bind to the three glucose residues present on the N-linked glycan core. Chaperone proteins typically aid in the folding of the protein to which the glycan is attached. Following proper folding, the three glucose residues are removed, and the N-linked glycan can move on to further processing reactions. If the protein fails to fold properly, the three glucose residues are reattached, allowing the protein to re-associate with chaperones. This cycle may repeat several times until a protein reaches it proper conformation. If a protein repeatedly fails to properly fold, it is usually excreted from the endoplasmic reticulum and degraded by cytoplasmic proteases.

Alternatively or additionally, N-linked glycans contribute to protein folding by steric effects. For example, cysteine residues in a peptide may be temporarily blocked from forming disulfide bonds with other cysteine residues, due to the size of a nearby glycan. Presence of an N-linked glycan, therefore, can allow a cell to control which cysteine residues will form disulfide bonds.

N-linked glycans can be involved in cell-cell interactions. For example, tumor cells frequently produce abnormal N-linked glycan structures, which can be recognized by the CD337 receptor on natural killer cells as a sign that the cell in question is cancerous.

N-linked glycans can be involved in targeting of degradative lysosomal enzymes to the lysosome. A modification of an N-linked glycan with a mannose-6-phosphate residue can serve as a signal that the protein to which this glycan is attached should be targeted to the lysosome.

2. O-Linked Glycans

O-linked oligosaccharide chains are added to specific serine or threonine residues in polypeptide chains. The transfer of the first sugar residue, which in many instances is an N-acetylgalactosamine, typically begins in the endoplasmic reticulum and is completed in the Golgi apparatus. The residues of an O-linked oligosaccharide are added one at a time and the addition of each residue is catalyzed by a specific enzyme. In contrast to N-linked glycosylation, the consensus amino acid sequence for O-linked glycosylation is less well defined.

3. Glycoconjugates

Techniques of the present disclosure may be applied to assess and/or enrich for unusually modified glycans on any glycoconjugate of interest (hereafter the "target glycoconjugate"). Reference to a "glycoconjugate of interest," "glycoprotein of interest," "target glycoconjugate," "target glycoprotein," etc. is not intended to imply that there is always one particular glycoconjugate whose glycans are being assessed. Indeed, in certain embodiments, provided methods are used to assess glycans from glycoconjugates present in a source material, without intending to target a particular glycoconjugate.

In certain embodiments, glycans on a particular glycoconjugate of interest are assessed. In some embodiments, the glycoconjugate of interest is a glycoprotein (hereafter the "target glycoprotein.").

In some embodiments, the target glycoconjugate is produced naturally by a cell. In some embodiments, the target glycoconjugate is not naturally produced by a cell; rather, a cell has been engineered to produce it. In some embodiments, the target glycoconjugate is naturally produced by a cell, but the cell has been engineered to produce it at an elevated level and/or under predetermined conditions (e.g., in the presence of an inducing agent, etc.)

In many embodiments, a target glycoconjugate has therapeutic activity when administered to animals (e.g., mammals such as humans). For example, erythropoietins, interferons, blood-clotting factors, colony stimulating factors, a variety of antibodies, and certain enzymes, among many others, are all glycoproteins that are currently produced in engineered cell lines as biopharmaceutical agents. In some embodiments, glycans on biopharmaceutical agents (such as, for example, those mentioned previously) are assayed as described herein. One of ordinary skill in the art will be aware of other commercially relevant glycoconjugates that can be expressed industrially (e.g., in production bioreactors) for therapeutic and other purposes. The present disclosure provides methods for assessing glycans of such commercially relevant glycoconjugates (e.g., glycoproteins).

Representative commercially available glycoprotein products include, for example, those listed in Table 1.

TABLE 1

| Non-limiting examples of commercially available glycoprotein products | |
|---|---|
| Protein Product | Reference Drug |
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betascron ® |
| Tositumomab | Bexxar ® |
| antihemophilic factor | Bioclate ™ |
| human growth hormone | BioTropin ™ |
| botulinum toxin type A | Botox ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune Fab, ovine | DigiFab ™ |
| Rasburicase | Elitek ® |
| Etanercept | Enbrel ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | Forteo ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | Hemofil ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| Palifermin | Kepivanee |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa, for injection | Luveris |
| OspA lipoprotein | LYMErix ™ |
| Ranibizumab | Lucentis ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| insulin; zinc suspension; | Novolin L ® |

TABLE 1-continued

Non-limiting examples of commercially available glycoprotein products

| Protein Product | Reference Drug |
|---|---|
| insulin; isophanc suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| human chorionic gonadotropin | Ovidrel ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| Lepirudin | Refludan ® |
| Infliximab | Remicade ® |
| Abeiximab | ReoPro ™ |
| Reteplase | Retavase ™ |
| Rituximab | Rituxan ™ |
| interferon alfa-2a | Roferon-A ® |
| Somatropin | Saizen ® |
| synthetic porcine secretin | SecreFlo ™ |
| Basiliximab | Simulect ® |
| Eculizumab | Soliris ® |
| Pegvisomant | Somavert ® |
| Palivizumab; recombinantly produced, humanized mAb | Synagis ™ |
| thyrotropin alfa | Thyrogen ® |
| Tenecteplase | TNKase ™ |
| Natalizumab | Tysabri ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

As will be appreciated by those of ordinary skill in the art, the glycosylation patterns (including modifications such as, for example, those discussed herein) of such therapeutic glycoproteins can potentially affect their therapeutic properties. In some embodiments, glycans of the therapeutic glycoproteins are assessed as the glycoproteins are being produced, i.e., at various stages of production. Such assessments may facilitate quality control.

Those of ordinary skill in the art will appreciate that the present disclosure is not limited to assessment of glycans on the above-listed glycoconjugates, or indeed on therapeutic glycoconjugates, or on glycoconjugates whose expression (and/or degree or timing of expression) has been engineered in a cell. These represent certain particular embodiments of the present disclosure; those of ordinary skill in the art will appreciate, however, that the principles of the disclosure apply to any target glycoconjugate.

B. Sources of Glycans and/or Glycoconjugates

Material that can be treated to obtain a glycan preparation generally comprises glycoconjugates (such as glycoproteins) whose glycans are to be analyzed and/or enriched. Materials can be obtained from a variety of sources including, but not limited to, therapeutic formulations (e.g., erythropoietin, insulin, human growth hormone, etc.), commercial biological products (e.g., those presented in Table 1), biorcactors, and biological samples. Materials may be obtained from one source or pooled from multiple sources. As used herein, the term "biological sample" refers to any solid or fluid sample (e.g., bodily fluids) obtained from, excreted by or secreted by any living cell or organism, including, but not limited to, tissue culture, human or animal tissue, plants, fruits, vegetables, single-celled microorganisms (such as bacteria and yeasts), multicellular organisms, and combinations thereof. For example, a biological sample can be a biological fluid obtained from, for example, blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, for example, a sample obtained from any organ or tissue (including a biopsy or autopsy specimen), can comprise cells (whether primary cells or cultured cells), medium conditioned by any cell, tissue or organ, tissue culture.

Source materials that can be treated to obtain a glycan preparation may be received by any machine, person, or entity. In some embodiments, source materials may be received by a machine, which may then perform one or more tests, processes, or refinements of the glycoprotein preparation. In some embodiments, source materials may be received by a person. In some embodiments, source materials may be received from an outside entity. In some embodiments, source materials may be received by a person or business performing characterization services for a second person or business. For example, a business may be operated in which the business receives source materials (that comprise glycans to be characterized) from other businesses or laboratories. Source materials that are suitable for treatment to obtain a glycan preparation may be preprocessed in any manner. For example, source materials may be preprocessed to isolate one or more glycoforms.

In certain embodiments, source materials comprise glycoconjugates (e.g., glycoproteins) that are produced by cells. Glycoproteins can be produced in any of a variety of cells and/or cell lines. Indeed, any cell that glycosylates at least some of its proteins can be used and grown under any conditions that allow such glycosylation to occur. Suitable cells include, but are not limited to, mammalian cells, avian cells, fish cells, insect cells, plant cells, fungal cells, bacterial cells, and hybrid cells. In some embodiments, the cells have been engineered (e.g., genetically and/or chemically) to have one or more glycosylation characteristics more similar to human cells.

Exemplary mammalian cells that can be used in accordance with the present disclosure include, but are not limited to, Chinese hamster ovary (CHO) cells, HeLa cells, Madin-Darby canine kidney (MDCK) cells, baby hamster kidney (BHK cells), NSO cells, MCF-7 cells, MDA-MB-438 cells, U87 cells, A172 cells, HL60 cells, A549 cells, SP10 cells, DOX cells, DG44 cells, HEK 293 cells, SHSY5Y, Jurkat cells, BCP-1 cells, COS cells, Vero cells, GH3 cells, 9L cells, 3T3 cells, MC3T3 cells, C3H-10T1/2 cells, NIH-3T3 cells, and C6/36 cells.

Exemplary fish cell lines that can be used in accordance with the present disclosure include, but are not limited to, ZF4 cells, AB9 cells, GAKS cells, OLF-136 cells, CAEP cells, CAF cells, OLHE-131 cells, OLME-104 cells, ULF-23 cells, BRF41 cells, Hepa-E1 cells, Hepa-T1 cells, GEM-81 cells, GEM-199 cells, GEM-218 cells, GAKS cells, D-11 cells, R1 cells, RTG-2 cells, RTO cells, and TPS cells. A more complete list can be found in Fryer and Lannan, 2005, "Three decades of fish cell culture: a current listing of cell lines derived from fishes," *J. Tissue Culture Methods*, 16:87-94.

Exemplary insect cell lines that can be used in accordance with the present disclosure include, but are not limited to, SFM cells, Sf21 cells, Sf9 cells, Schneider cells, S2 cells, T.ni cells, SES-MaBr-1 cells, SES-MaBr-3 cells, NIAS-MB-25 cells, NIAS-MaBr-92 cells, FRI-SpIm-1229 cells, SES-MaBr-4 cells, NIAS-LeSe-11 cells, TUAT-SpLi-221 cells, NIAS-PX-64 cells, NIAS-MB-32 cells, NIAS-MaBr-93 cells, SES-MaBr-5 cells, BM-N cells, NIAS-PX-58 cells, MBHL-2 cells, and MBHL-3 cells.

Those of ordinary skill in the art will recognize that this is an exemplary, not a comprehensive, listing of various cells that may be used in accordance with the present disclosure.

Other cells may be advantageously utilized to produce a target glycoprotein. Such cells may be in culture or in the context of a tissue, organ, or organism.

Those skilled in the art will also appreciate that a variety of expression systems and vectors may be used in order to express a protein of interest within cells or cell lines used in accordance with the present disclosure (e.g., see *Molecular cloning: A Laboratory Manual*, Ed. by Sambrook, CSHL Press, 2002).

Also, any of a variety of cell culture media, including complex media and/or serum-free culture media, that are capable of supporting growth of the one or more cell types or cell lines may be used in accordance with the present disclosure. Typically, a cell culture medium contains a buffer, salts, energy source, amino acids (e.g., natural amino acids, non-natural amino acids, etc.), vitamins and/or trace elements. Cell culture media may optionally contain a variety of other ingredients, including but not limited to, carbon sources (e.g., natural sugars, non-natural sugars, etc.), cofactors, lipids, sugars, nucleosides, animal-derived components, hydrolysates, hormones/growth factors, surfactants, indicators, minerals, activators/inhibitors of specific enzymes, and organics (e.g., butyrate, which induces apoptosis, which releases glycosylases, often slows down growth rate of cell, which changes glycosyltransferase levels, which can result in more mature glycosylation; and results in change in energy of cell; chloroquin, which affects intracellular pH; betaine, an osmoprotectant; ammonia, which alters intracellular pH levels and which can change glycosyl transferase efficiency; etc.), and/or small molecule metabolites (e.g., CMP-sialic acid, glucosamine, non natural sugar derivatives, etc.). Cell culture media suitable for use in accordance with the present disclosure are commercially available from a variety of sources, e.g., ATCC (Manassas, Va.).

In certain embodiments, one or more of the following media are used to grow cells: RPMI-1640 Medium, Dulbecco's Modified Eagle's Medium, Minimum Essential Medium Eagle, F-12K Medium, Iscove's Modified Dulbecco's Medium. As will be understood by those of ordinary skill in the art, when defined medium that is serum-free and/or peptone-free is used, the medium is typically highly enriched for amino acids and trace elements (see, for example, U.S. Pat. No. 5,122,469 to Mather et al., and U.S. Pat. No. 5,633,162 to Keen et al.).

Different cell culture media may affect the glycosylation pattern of glycoproteins expressed in the media. For example, a given cell culture medium may result in production of glycoproteins with an increased glycosylation pattern, a decreased glycosylation pattern, or an altered glycosylation (e.g., representing an increase in certain glycans and a decrease in others). One of ordinary skill in the art will be aware of and will be able to choose one or more suitable cell culture media for use in growing cells whose glycans are to be analyzed using certain methods of the present disclosure.

In some embodiments, cells are cultured in batch culture, fed batch culture, perfusion culture, static suspension (e.g., roller bottles, T flasks, microcarriers, T150, etc.), and/or on shakers.

Cells that produce at least one glycoprotein (i.e., target glycoprotein) according to the present disclosure can be grown under any of a variety of cell culture conditions.

In some embodiments, cells are cultured under conditions such that the target glycoprotein is expected to exhibit a desired glycosylation pattern. In some embodiments, one or more cell culture conditions are controlled and/or modified in order to produce the target glycoprotein with a more desirable glycosylation patterns. Such cell culture conditions that can be controlled or modified include, but are not limited to, pH, $CO_2$ levels, oxygen levels, culture agitation rate, redox conditions, culture temperature, cell density, density of seed culture, duration of culture, reactor design, sparge rate, and/or osmolarity.

Any of a variety of methods can be used to isolate cells from the cell culture medium, if desired. In certain embodiments, cells are grown in a suspension culture. In such embodiments, cells may be purified from the cell culture medium by one or more cycles of centrifugation and washing (e.g., with a physiological suitable washing solutions such as phosphate-buffered saline).

In certain embodiments, cells are grown in an adhesion culture. In such embodiments, cells may be purified from the cell culture medium by first releasing them from the culture surface. For example, cells may be released from the culture surface by subjecting them to EDTA. Those of ordinary skill in the art will be aware of other suitable agents that can be used to release adherent cells from the culture surface. After release, cells may be purified by one or more cycles of centrifugation and washing (e.g., with a physiological suitable washing solutions such as phosphate-buffered saline). As with cells grown in suspension culture, care may be taken not to centrifuge the cells with too much force in order to avoid unnecessary cell breakage.

C. Treatment

Source materials comprising glycoconjugates are then subjected to a dual treatment as described below. "Glycan preparations from which sialic acids have been released" as used herein refers to the resulting preparation after dual treatment and optional additional processing (such as, for example, additional treatments, storage, fractionation, freezing, thawing, etc.)

Dual treatments used in preparing glycan preparations generally comprise (1) a treatment to release glycans from glycoconjugates and (2) a treatment to release sialic acids. Treatments can be performed in any order relative to one another, including simultaneous and/or overlapping treatments. For example, glycans can be released from glycoconjugates and then treated to release sialic acids (e.g., with sialidase). In some embodiments, glycoconjugates are treated to release sialic acids (e.g., with sialidase) and then glycans are released from glycoconjugates. In some embodiments, glycoconjugates are subjected to both treatments at the same time during at least part of total duration of the dual treatments.

1. Release of Glycans

Glycans are released from glycoconjugates using any of a variety of methods such as methods described herein.

In certain embodiments, one or more glycan structures is/are cleaved from glycoconjugates after the glycoconjugates have been liberated from a cell (e.g., through treatment with proteases, as described in more detail below). In certain embodiments, one or more glycan structures are cleaved from glycoconjugates (such as glycoconjugates on a cell surface) that have not been liberated from a cell.

In certain embodiments, one or more glycan structures are released through the use of an enzyme or plurality of enzymes that recognizes and cleaves the glycan structures. Any of a variety of glycosidic and other enzymes that cleave glycan structures from glycoconjugates may be used in accordance with the present disclosure. Several examples of such enzymes are reviewed in R. A. O'Neill, *Enzymatic release of oligosaccharides from glycoproteins for chromatographic and electrophoretic analysis*, J. Chromatogr. A 720, 201-215. 1996; and S. Prime, et al., *Oligosaccharide sequencing based on exo- and endo-glycosidase digestion and liquid chromatographic analysis of the products*, J. Chromatogr. A 720, 263- 274, 1996, each of which is incorporated herein by reference in its entirety. In certain embodiments, the enzyme PNGase F (Peptide N-Glycosidase F) is used to remove glycans from a glycopeptide or glycoprotein. PNGase F is an amidase that cleaves the amide bond between the innermost GlcNAc and asparagine residues of high mannose, hybrid, and complex oligosaccharides from N-linked glycoproteins. Additionally or alternatively, in certain embodiments, the enzymes PNGase A, O-glycanase, and/or Endo-H are used to remove glycans.

To improve the accessibility of the glycosylation site in a glycoprotein to a cleavage enzyme, some glycoproteins may undergo a protein denaturation step. Typically, protein denaturation is accomplished by using detergents (e.g., SDS) and/or disulfide-reducing agents (e.g., beta-mercaptoethanol), although methods of denaturing a glycoprotein for use in accordance with the present disclosure are not limited to the use of such agents. For example, exposure to high temperature can be sufficient to denature a glycoprotein such that a suitable enzyme for cleaving glycan structures is able to access the cleavage site. In certain embodiments, a glycoprotein is denatured by incubating the glycoprotein at temperature of about 80, about 81, about 82, about 83, about 84, about 85, about 86, about 87, about 88, about 89, about 90, about 91, about 92, about 93, about 94, about 95, about 96, about 97, about 98, about 99, about 100 degrees Celsius, or higher for a period of time sufficient to denature the glycoprotein.

In certain embodiments, a combination of detergents, disulfide-reducing agents, high temperature, and/or other agents or reaction conditions is employed to denature a glycoprotein. Those of ordinary skill in the art will be aware of suitable conditions, incubation times, etc. that will be sufficient to denature a glycoprotein. It is noted that oligosaccharides located at conserved Fc sites in immunoglobulin G (IgG) are easily cleaved by PNGase F. Thus, a protein denaturation step is typically not required for IgG molecules when this enzyme is used. PNGase F is also capable of removing oligosaccharides in dilute ammonium hydroxide solution, is stable in 2.5 M urea at 37° C. for 24 h, and still possesses 40% of its activity in 5 M urea. Thus, PNGase F has the advantage that it is capable of cleaving glycans from glycoproteins under certain denaturation conditions.

Other suitable enzymes that can be used to cleave glycan structures from glycoconjugates in accordance with the present disclosure include, but are not limited to, PNGase A, O-glycanase and/or Endo-H. Those of ordinary skill in the art will be aware of other suitable enzymes for cleavage of glycans from glycoconjugates. In some embodiments, a plurality of enzymes is used to cleave glycan structures from a glycoconjugate. In some embodiments, such a plurality of cleavage enzymes is administered simultaneously. In some embodiments, such a plurality of cleavage enzymes is administered sequentially.

In some embodiments, one or more glycan structures are cleaved from glycoconjugates through the use of an agent other than an enzyme. In some embodiments, a chemical agent or plurality of chemical agents (e.g., exposure to an agent such as hydrazine, sodium borohydride, endoglycosidases, trifluoromethasenulfonic acid (TFMS), and/or beta-elimination, etc) can be used to cleave glycan structures from glycoconjugates. For example, use of the chemical hydrazine has been successfully employed to cleave glycan structures. As another non-limiting example, it has been suggested that a mixture of ammonia-ammonium carbonate can be used for alkaline release of both the N- and O-linked oligosaccharides in their native form (see Y. Huang, et al., *Microscale nonreductive release of O-linked glycans for subsequent analysis*

*through MALDI mass spectrometry and capillary electrophoresis*, Anal. Chem. 73, 6063-60, 2001, incorporated herein by reference in its entirety). Those of ordinary skill in the art will be aware of other suitable chemical agents that can be used in accordance with the present disclosure. In some cases, use of a chemical agent to cleave glycan structures from a glycoprotein results in protein degradation as well as cleavage. However, after cleavage, the glycan structure is often purified away from the protein component of the glycoprotein before analysis and/or characterization. In such situations, degradation of the protein component after treatment with a chemical agent is not detrimental to the practice of the present disclosure. In some cases, degradation of the protein component may even aid in the process of purifying the cleaved glycan structure(s).

2. Release of Sialic Acids

Providing a glycan preparation from which sialic acids have been released generally comprises exposing a composition comprising glycans (released or in the context of glycoconjugates, or both) to one or more agents that cleave sialic acid residues, under conditions that allow cleavage of sialic acid residues. Any of a variety of agents that cleave sialic acid residues from glycans may be used in accordance with provided methods.

In some embodiments, releasing sialic acids from a glycan preparation comprises treatment with a sialidase. Sialidase treatment may be accomplished, for example, using an enzyme polypeptide with sialidase activity, chemicals (e.g., mild acids, etc.), or a combination thereof.

In some embodiments, sialidase treatment is accomplished using one or more enzyme polypeptides capable of cleaving linkages of sialic acids (for example, capable of hydrolyzing glycosidic linkages of sialic acids, capable of endohydrolyzing (2→8)-α-sialosyl linkages in oligo- or poly(sialic) acids, and/or capable of eliminating α-sialyl groups in N-acetylneuraminic acid glycosides). Such enzymes are typically known as sialidases and/or neuraminidases. Typically, a particular sialidase enzyme preferentially cleaves a particular kind of sialic acid linkage.

Enzyme polypeptides that may be appropriate for use include, but are not limited to, exo-α-sialidases (also known as acetylneuraminyl hydrolase, α-neuraminidase, or acetylneuraminidase; including enzyme polypeptides classified under E.C. 3.2.1.18), endo-α-sialidases (also known as polysialoside 2,8-α-sialosylhydrolase, endo-N-acylneuraminidase, endoncuraminidase, endo-N-acetylneuraminidase, poly(α-2,8-sialosyl) endo-N-acetylneuraminidase, poly(α-2,8-sialoside) α-2,8-sialosylhydrolase, or endosialidase; including enzyme polypeptides classified under E.C. 3.2.1.129, and anhydrosialidase (also known as anhydroneuraminidase, sialglycoconjugate N-acylneuraminylhydrolase (2,7-cyclizing), or sialidase L).

Non-limiting specific examples of sialidase enzymes include sialidase 1 (also known as lysosomal sialidase, NEU1, or neuraminidase 1), sialidase 2 (also known as cytosolic sialidase, NEU2, or neuraminidase 2), sialidase 3 (also known as membrane sialidase, NEU3, or neuraminidase 3), sialidase 4 (also known as NEU4 or neuraminidase 4), G9 sialidase, ganglioside sialidase, ganglioside-specific sialidase, hemagglutinin-neuraminidase protein, mouse skeletal muscle sialidase, N-acetylneuraminosyl glycohydrolase, N-acylneuraminate glycohydrolase, SA85-1.1 protein, SA85-1.2 protein, SA85-1.3 protein, sialidase A, sialidase C, sialidase S, and trans-sialidase.

Enzymes polypeptides suitable for use in sialidase treatment may be obtained from a variety of sources, including, but not limited to, naturally occurring sources, recombinantly engineered species, etc. Variants of known and/or naturally occurring sialidase enzymes may be used. A variety of species (including, but not limited to, *Arthrobacter nicotianae, Arthrobacter* sp., *Arthrobacter ureafaciens*, bacteriophage E, bacteriophage K1E, bacteriophage K1F, bacteriophage PK1A, bacteriophage PK1F, *Clostridium perfringens, Clostridum chauvoei, Clostridum sordellii, Corynebacterium diphtherias, Corynebacterium ulcerans, Crassostrea virginica, Cricetulus griseus, Entamoeba histolytica, Erysipelothrix rhusiophatiae, Homo sapiens*, influenza A virus, influenza B virus, *Macrobdella decora, Micromonas viridifaciens*, Mumps virus, mus musculus, Newcastle disease virus, *Pasteurella multocida, Streptococcus* sp., *Trichomonas vaginalis, Pasteurella multocida, Streptococcus* sp., *Sus scrofa, Trichomonas vaginalis, Trypanosoma cruzi*, and *Vibrio cholerae*) produce enzyme sialidases that can be produced and/or used in accordance with provided methods.

As is known in the art, enzymes that are not known and/or listed in enzyme databases (such as, for example, enzymes that are not yet characterized), but nevertheless cleave linkages of sialic acid residues, may be suitable for use in accordance with provided methods and systems.

Appropriate conditions for treatment with enzymes polypeptides may vary depending on the particular enzyme polypeptide. Typically, a glycan-containing sample is incubated at or near the optimal temperature for the enzyme polypeptide in the presence of a concentration of enzyme polypeptide sufficient to catalyze a desired amount of cleavage for a given period of time. For example, some incubations may be performed at about 37° C. Incubation periods may last about 5 minutes, 10 minutes, 20 minutes, 25 minutes, 30 minutes, 35 minutes, 40 minutes, 45 minutes, 50 minutes, 55 minutes, 1 hour, 1 hour and 10 minutes, 1 hour and 20 minutes, 1 hour and 30 minutes, 1 hour and 40 minutes, 1 hour and 50 minutes, 2 hours, 2.5 hours, 3 hours, 3.5 hours, 4 hours, 4.5 hours, 5 hours, 5.5 hours, 6 hours, or more. In some embodiments, glycan-containing samples may be incubated with enzyme polypeptides overnight.

Any combination of sialidase enzymes as mentioned herein and/or of their variants may be used for sialidase treatment. Treatment using more than one enzyme may be sequential (i.e., one enzyme polypeptide incubation followed by another, optionally separated by inactivation of one enzyme), and/or simultaneous (i.e., more than one enzyme polypeptide used at the same time).

In some embodiments, sialidase treatment is accomplished using one or more chemicals. For example, mild acid hydrolysis of sialic acid residues can be performed using any of a variety of methods known in the art. Generally, mild acid hydrolysis comprises incubating a sample with a dilute acid for a short period of time, optionally with heat. Non-limiting examples of acids that are used in mild acid hydrolysis include sulfuric acid ($H_2SO_4$), hydrochloric acid (HCl), formic acid ($CH_2O_2$), etc. The pHs of acid solutions used in mild acid hydrolysis typically range from about pH 1.4 to about pH 6.9, for example about pH 6.9, pH 6.8, pH 6.7, pH 6.6, pH 6.5, pH 6.4, pH 6.3, pH 6.2, pH 6.1, pH 6.0, pH 5.9, pH 5.8, pH 5.7, pH 5.6, pH 5.5, pH 5.4, pH 5.3, pH 5.2, pH 5.1, pH 5.0, pH 4.9, pH 4.8, pH 4.7, pH 4.6, pH, pH 4.5, pH 4.4, pH 4.3, pH 4.2, pH 4.1, pH 4.0, pH 3.9, pH 3.8, pH 3.7, pH 3.6, pH, pH 3.5, pH 3.4, pH 3.3, pH 3.2, pH 3.1, pH 3.0, pH 2.9, pH 2.8, pH 2.7, pH 2.6, pH, pH 2.5, pH 2.4, pH 2.3, pH 2.2, pH 2.1, pH 2.0, pH 1.9, pH 1.8, pH 1.7, pH 1.6, pH 1.5, or pH 1.4. Lower pH conditions may be used in some embodiments. Concentrations of acids used in mild acid hydrolysis treatments may be, for example, about 0.70 M, 0.65 M, 0.60 M, 0.55 M, 0.50 M, 0.45 M, 0.40 M, 0.35 M, 0.30 M, 0.25 M, 0.20 M, 0.15 M, 0.10 M, 0.05 M, 0.025 M, 0.020 M. 0.015 M, 0.010 M, 0.005 M, or less. Higher concentrations of acids may be used in some embodiments. Incubation in mild acid can be performed for a period of time such as less than about 10.0 hours, 9.5 hours, 9.0 hours, 8.5 hours, 8.0 hours, 7.5 hours, 7.0 hours, 6.5 hours, 6.0 hours, 5.5 hours, 5.0 hours, 4.5 hours, 4.0 hours, 3.5 hours, 3.0 hours, 2.5 hours, 2.0 hours, 1.5 hours, 1.0 hours, 50 minutes, 45 minutes, 40 minutes, 35 minutes, 30 minutes, 25 minutes, 20 minutes, 15 minutes, 10 minutes, 5 minutes, 1 minute, or less. Glycan-containing samples may be incubated for longer periods of time in some embodiments.

In some embodiments in which mild acid hydrolysis is used, glycan-containing samples are heated during mild acid treatment. Samples may be heated at temperatures such as, for example, about 30° C., 35° C., 40° C., 45° C., 50° C., 55° C., 60° C., 65° C., 70° C., 75° C., 80° C., 85° C., 90° C., 95° C., 100° C., or greater.

In some embodiments, treatment to release sialic acids results in substantial desialylation of glycans. As is understood in the art, not all sialic acid residues may be released from a glycan molecule that has undergone treatment to release sialic acids. In some embodiments, treatment to release sialic acids leaves up to about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less of the sialic acid residues present in the glycan preparation before treatment to release sialic acids. In some embodiments, such residual sialic acid residues do not interfere with subsequent treatment and/or analyses. In some embodiments, additional treatment(s) are used to lower the percentage of residual sialic acids before subsequent treatment and/or analyses; in some such embodiments, additional treatment(s) comprise one or more additional treatments to release sialic acids.

In some embodiments, compositions comprising glycans include sialic acids that are modified in such a way as to render them resistant to treatment to release sialic acids; in some such embodiments, the modifications render the sialic acids resistant to cleavage by sialidases An example of such a modification is acetylation at two or more positions in addition to the 5 position (which is typically acetylated), termed "multi-acetylated sialylation" as described further below. When a composition comprising glycans contains such modified sialic acids, the residual percentage of sialic acid residues may be higher.

3. Release of Glycoconjugates from Cells

In certain embodiments, such as those involving using glycoconjugates produced by cells, methods further comprise releasing glycoconjugates from cells. In some such embodiments, glycans are released from glycoconjugates after glycoconjugates are released from cells.

In some embodiments, glycoconjugates that are present within cells are released.

In some embodiments, glycans are released from glycoconjugates that are present on surfaces of cells. In some such embodiments, glycan preparations are obtained from glycoconjugates that are primarily released from the surface of the cell. Among the several advantages offered by such embodiments is the fact that a highly pure population of cell-surface glycans can be obtained without significant contamination by glycans that are primarily found inside the cell. For example, using certain methods of the present disclosure, lysis of cells is substantially avoided when cell-surface glycans are liberated from the cell. Additionally or alternatively, certain methods disclosed herein offer significant reductions in the number and/or difficulty of manipulation steps as compared to currently available methods.

In certain embodiments, glycoconjugates are released from cells by subjecting the cells to one or more proteases. Proteases cleave amide bonds within a polypeptide chain. Several classes of proteases exist including both chemical and enzymatic agents. Proteolytic enzymes include, for example, serine proteases, threonine proteases, cysteine proteases, aspartic acid proteases, metalloproteases, and glutamic acid proteases. Non-limiting examples of specific proteolytic enzymes that can be used in accordance with the present disclosure include trypsin, chymotrypsin, elastase, subtilisin, proteinase K, pepsin, ficin, bromelin, plasmepsin, renin, chymosin, papain, a cathepsin (e.g. cathepsin K), a caspase (e.g. CASP3, CASP6, CASP7, CASP14), calpain 1, calpain 2, hermolysin, carboxypeptidase A or B, matrix metalloproteinase, a glutamic acid protease, and/or combinations thereof. Those of ordinary skill in the art will be aware of a number of other proteases that can be used in accordance with the present disclosure to release a glycoprotein from the surface of a cell.

In some embodiments, cell surface glycoconjugates are released from membranes. In some such embodiments, one or more harsh detergents is/are used to extract membrane-bound glycoconjugates, after which free sugars are dialyzed away before treatment to release glycans from glycoconjugates. In some embodiments in which glycoconjugates are released from membranes, detergent treatment is minimized or avoided altogether to minimize disruption of cell membranes. For example, in some embodiments, at least 80%, 85%, 90%, 95%, 96%, 97%, 98%, 99%, or more of the cell membranes remain intact (e.g., as monitored by trypan blue exclusion). Such methods may be used to can reduce or eliminate contamination from immature, high-mannose glycoproteins that are present inside the cell.

In some embodiments, cells are subject to one or more proteases under conditions that minimize disruption of the cell membrane. In some embodiments, cells are exposed to one or more proteases for a limited period of time in order to avoid substantial lysis of the cell membrane.

For example, a cell may be subjected to one or more proteases for a period of time that is less than about 15, 14, 13, 12, 11, 10, 9, 8, 7, 6, 5, 4, 3, 2, or 1 minute(s). In some embodiments, a cell is subjected to one or more proteases for a period of time that is more than 15 minutes so long as substantial lysis of the cell membrane does not occur. For example, a sufficiently low concentration of protease(s), a sufficiently low temperature and/or any of a variety of other factors or conditions may be employed such that the overall protease activity is decreased to a point where substantial lysis of the cell membrane does not occur. Those of ordinary skill in the art will be aware of and will be able to employ factors or conditions that ensure that substantial lysis of the cell membrane does not occur.

In some embodiments, at least about 50%, 60%, 70%, 80%, 90%, 91%, 92%, 93%, 94%, 95%, 96%, 97%, 98%, 99% or more glycoconjugates are released from cells, for example by treatment with a protease.

In certain embodiments, glycoconjugates are released by subjecting a cell to one or more proteases (e.g., proteolytic enzymes) at a concentration of at least about 0.1 mg/mL. In certain embodiments, glycoconjugates are released by subjecting a cell to one or more proteases (e.g., proteolytic enzymes) at a concentration of less than about 2.0 mg/mL. In certain embodiments, cell surface glycans are released by subjecting a cell to one or more proteases (e.g., proteolytic enzymes) at a concentration of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 5.0, 6.0, 7.0, 8.0, 9.0, 10.0 mg/mL or higher.

In certain embodiments, glycoconjugates are released by subjecting a cell to a plurality of proteases. For example, a cell may be subjected to 2, 3, 4, 5, 6, 7, 8, 9, 10, or more proteases to release glycoconjugates. Such a plurality of proteases may be administered to the cell simultaneously and/or sequentially. In certain embodiments, glycoconjugates are released by subjecting a cell to a plurality of proteases simultaneously, after which the released glycoconjugates are purified away from the cell.

In certain embodiments, glycoconjugates are released by subjecting a cell to a first protease (or plurality of first proteases) for a first period of time, after which the cell is subjected to a second protease (or plurality of second proteases) for a second period of time. Prior to treatment with the second protease, the first protease may optionally be removed and/or inactivated. By way of example, the first protease may be inactivated incubating the protease at a temperature for a time sufficient to inactivate it. Additionally or alternatively, the first protease may be inactivated by incubating it with an inhibitor that is specific to the protease (e.g. an antibody or other molecule that specifically binds the first protease and inhibits its catalytic activity). Other methods of inactivating the first protease will be known to those of ordinary skill in the art. In the case where the first protease is inactivated by incubating it with a specific inhibitor, it will be appreciated that the presence of the inhibitor should not substantially inhibit the activity of the second protease.

In some embodiments, the protease(s) are removed and/or inactivated prior to release of glycans. By way of example, a protease may be inactivated incubating the protease at a temperature for a time sufficient to inactivate it. Alternatively or additionally a protease may be inactivated by incubating with an inhibitor or antibody or other molecule that specifically binds to the protease and inhibits its catalytic activity.

4. Additional Exoglycosidase Treatment

In some embodiments, glycans are digested with one or more exoglycosidases, in addition to undergoing treatment to release glycans and treatment to release sialic acids as mentioned above. In some such embodiments, digestion products of such additional exoglycosidase treatments are analyzed in accordance with provided methods.

As mentioned above, sialidases are typically classified as exoglycosidases. Optional additional exoglycosidase treatments generally comprise treatment with at least one exoglycosidase other than sialidase. In some embodiments, one or more sialidases are used in combination with one or more other exoglycosidases that are not sialidases.

In some embodiments, additional exoglycosidase treatment is performed simultaneously with or overlapping with glycan release treatment and/or treatment to release sialic acids. In some embodiments, additional exoglycosidase treatment is performed before sialidase treatment. In some embodiments, additional exoglycosidase treatment is performed after sialidase treatment.

Exoglycosidases are enzymes that cleave terminal glycosidic bonds from the non-reducing end of glycans. They are typically highly specific to particular monosaccharide linkages and anomericity ($\alpha/\beta$). In some embodiments, neighboring branching patterns can affect exoglycosidase specificity. Exoglycosidase treatment usually results in glycans of standard antennary linkages being cleaved down to the pentasaccharide core (M3N2) containing 3 mannose and 2 glcNAc residues. However, certain glycan species (e.g. antennary fucosylated species, high-mannose and hybrid glycans, lactosamine-extended glycans, phosphorylated glycans, sulfated glycans, multi-acetylated sialylated glycans, etc.) may be resistant to exoglycosidase treatment and can be chromatographically resolved and quantified relative to the M3N2 pentasaccharide, as discussed herein.

In some embodiments, exoglycosidases used in accordance with the present disclosure recognize and cleave only one particular type of glycosidic linkage. In some embodiments, exoglycosidases used in accordance with the present disclosure recognize and cleave more than one particular type of glycosidic linkage. Exemplary exoglycosidases that can be used in accordance with the present disclosure include, but are not limited to, sialidase, galactosidase, hexosaminidase, fucosidase, and mannosidase. Exoglycosidases can be obtained from any source, including commercial sources (e.g. from QA-Bio, ProZyme, Roche, Sigma, NEB, EMD, Glyko, etc.). Alternatively or additionally, exoglycosidases can be isolated and/or purified from a cellular source (e.g. bacteria, yeast, plant, etc.).

Exoglycosidases (e.g. sialidases, galactosidases, hexosaminidases, fucosidases, and mannosidases) can be divided into multiple categories or "subsets." In some embodiments, the different subsets display different abilities to cleave different types of linkages. Table 1 presents some exemplary exoglycosidases, their linkage specificities, and the organism from which each is derived. One of ordinary skill in the art will appreciate that this is an exemplary, not a comprehensive, list of exoglycosidases, and that any exoglycosidase having any linkage specificity may be used in accordance with the present disclosure.

TABLE 1

Exemplary exoglycosidases

| Enzyme class | EC #* | Activity | Organism |
|---|---|---|---|
| α-Sialidase | 3.2.1.18 | α-2/3,6,8 (usually not linkage-specific) | Arthrobacter ureafaciens<br>Vibrio cholerae<br>Clostridium perfringens |
|  |  | α-2,3 (NeuAc from oligosaccharides) | Salmonella typhimurium<br>Streptococcus pneumonia |
|  |  | α-2/3,6 (NeuAc from complex) | Clostridium perfringens |
| β-Galactosidase | 3.2.1.23 | β-1/3,4,6 Gal linkages | Bovine testis<br>Xanthamonas species<br>Streptococcus species<br>E. coli |
|  |  | β-1/4,6 Gal linkages | Jack bean |
|  |  | β-1,4 Gal linkage | Streptococcus pneumonia |
|  |  | β-1,3-Gal linkage | E. coli<br>Xanthomonas species |
|  |  | β-1/3,6-Gal linkages | Xanthomonas species<br>E. coli |

TABLE 1-continued

Exemplary exoglycosidases

| Enzyme class | EC #* | Activity | Organism |
|---|---|---|---|
| β-Hexosaminidase | 3.2.1.52<br>3.2.1.30 | β-1/2,3,4,6 hexosamines | *Streptococcus plicatus*<br>*Streptococcus pneumonia*<br>*Bacteroides*<br>Jack bean |
| α-Fucosidase | 3.2.1.51<br>3.2.1.111 | α-1-3,4-Fuc (usually de-<br>glycosylate Lewis structure)<br>α-1/2,3,4,6-Fuc (usually has broad specificity)<br>α-1,6-Fuc<br>α-1,2-Fuc | *Xanthomonas*<br>Almond meal<br>Bovine kidney<br>*C. meningosepticum*<br>*E. coli*<br>*Xanthomonas* |
| α-Mannosidase | 3.2.1.24 | α-1/2,3,6-Man<br>α-1/2,3-Man<br>α-1,6-Man (typically a core mannosidase)<br>α-1,2-Man | Jack bean<br>*Xanthomonas manihotis*<br>*Xanthomonas* species<br>*Aspergillus saitoi* |
| β-Mannosidase | 3.2.1.25 | α-1,4-Man | *Helix pomatia* |

*"EC #" refers to Enzyme Commission registration number

According to the present disclosure, glycans (such as, for example, those that have been released from a glycoprotein and/or a cell surface) can be digested with any exoglycosidase. In certain embodiments, glycans are digested by subjecting a population of glycans to a plurality of exoglycosidases. For example, a population of glycans may be subjected to 2, 3, 4, 5, 6, 7, 8, 9, 10, or more exoglycosidases. In some embodiments, multiple exoglycosidases are administered simultaneously. In some embodiments, multiple exoglycosidases are administered sequentially. In some embodiments, varying the identity of the exoglycosidases which are administered reveals information about glycan structure and/or composition. In some embodiments, varying the sequence in which multiple exoglycosidases are administered reveals information about glycan structure and/or composition.

In some embodiments, sequential digestion with multiple exoglycosidases reveals information about glycan structure and/or composition that is different from information revealed by simultaneous digestion with the same set of exoglycosidases. In some embodiments, sequential digestion with multiple exoglycosidases reveals information about glycan structure and/or composition that is the same information revealed by simultaneous digestion with the same set of exoglycosidases. For a more complete discussion of the utility of exoglycosidase digestion in the analysis of glycan structure, see co-pending International Application No. PCT/US08/60343, filed Apr. 15, 2008, by Parsons et al., entitled "CHARACTERIZATION OF N-GLYCANS USING EXOGLYCOSIDASES," the entire contents of which are hereby incorporated by reference.

D. Glycan Preparations from which Sialic Acids have been Released

After dual treatment (treatment to release glycans and treatment to release sialic acids) discussed above, glycan preparations from which sialic acids have been released may be used with provided methods.

In certain embodiments, glycan preparations from which sialic acids have been released comprise glycans that are not sialylated.

In certain embodiments, glycan preparations from which sialic acids have been released comprise sialidase-resistant glycans.

In certain embodiments, glycan preparations from which sialic acids have been released comprise unusually modified glycans. Generally, unusually modified glycans bear modifications other than sialylation. In many embodiments, the unusual modifications impart a charge onto the glycans; in some such embodiments, the charge is a negative charge.

In some embodiments, unusually modified glycans comprise phosphorylated glycans. A non-limiting example of a phosphorylated residue in glycans is mannose-6-phosphate (Man-6-P).

In some embodiments, unusually modified glycans comprise sulfated glycans. Sulfation on glycans can occur at any of a variety of positions. Glycans can by singly and/or multiply sulfated (i.e., sulfated at multiple positions on a given glycan molecule). Non-limiting examples of positions known to be sulfated in some glycan species include the C-3 of a terminal Gal and the C-6 of a GlcNAc residue of a terminal N-acetyllactoasmine unit. Sulfated glycans include sulfated glycosaminoglycans such as heparan sulfate, dextran sulfate, keratan sulfate, and chondroitin sulfate.

In some embodiments, unusually modified glycans comprise sialylated glycans that have additional modifications that render the sialic acid residues resistant to cleavage by sialidases. For example, glycan preparations may comprise multi-acetylated sialylated glycans. Sialic acids residues are typically acetylated at the 5 position (see FIG. 2); such 5-acetylated sialic acids are typically sensitive to sialidase treatment. The applicants have discovered that sialic acids that are acetylated at two or more additional positions (multi-acetylated sialic acid) are generally resistant to sialidase treatment. In some embodiments, multi-acetylated sialic acids are acetylated at two or more of the 7, 8, and 9 positions (see FIG. 2).

In some embodiments, glycan preparations from which sialic acids have been released comprise glycans that have no modifications (whether sialylation and/or unusual modifications discussed herein).

In some embodiments, unusually modified glycans are low-abundance glycans. For example, in some embodiments, unusually modified glycans comprise less than about 50%, 40%, 30%, 20%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.08%, 0.05%, or less of the glycan preparation. In some embodiments, sialidase-resistant glycans comprise about 0.01% of the glycans. In some embodiments, unusually modified glycans comprise less than about 50%, 40%, 30%, 20%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.08%, 0.05%, or less of the total population of glycans in a source preparation (and/or in the original source material). In some embodiments, unusually modified glycans comprise about 0.01% of the total population of glycans in the source preparation and/or material.

II. Analysis of Glycan Preparations

According to provided methods, glycan preparations from which sialic acids have been released (e.g., sialidase-treated glycan preparations) comprise glycans that are not released by such treatment (e.g., sialidase-resistant glycans) and are subjected to one or more separation techniques that separate glycans having a first charge from uncharged glycans and/or glycans having a second charge, and/or that separate glycans based on charge-to-mass ratio. In some embodiments, at least one separated glycan (e.g., glycans having a first charge or having a first charge-to-mass ratio) are quantified using at least one quantification standard. In certain embodiments, additional analyses are performed on separated glycans (e.g., on glycans having the first charge and/or having the first charge-to-mass ratio) before and/or after quantification. In some embodiments, separated glycans are identified using information obtained during separation step(s), optional analysis step(s), or a combination thereof. In some embodiments, steps of separating, analyzing, and/or quantifying separated glycan species (such as, for example, unusually modified glycan species) in a sample are repeated and data from such iterations are entered into a database, e.g., as described below. In some embodiments, identifying glycan species (such as unusually modified glycans) may rely wholly or in part on information in the database.

A. Separation of Charged Glycans

A variety of methods are known in the art to separate a charged molecule from uncharged and/or oppositely charged molecules within a sample and/or from other molecules with different charge-to-mass ratios. Any of these methods, and variations thereof, can be used to separate glycans according to the present disclosure. In some embodiments, glycans having a first charge and/or having a first charge-to-mass ratio are isolated from the rest of the glycan preparation.

In some embodiments, glycans having a particular first charge-to-mass ratio are separated from glycans having a lower first charge-to-mass ratio. In some embodiments, glycans having a particular first charge-to-mass ratio are separated from glycans having a higher first charge-to-mass ratio.

In some embodiments, the first charge-to-mass ratio has an absolute value within the range of about 0 to about 0.0014, and glycans having such first charge-to-mass ratio are separated from other glycans whose charge-to-mass ratios have an absolute value within the range of about 0 to about 0.003.

In some embodiments, glycans having a first charge are isolated from the rest of the glycan preparation.

In certain embodiments, the first charge is a negative charge and the second charge is a positive charge. In such embodiments, separated glycans comprise negatively charged glycans, which are separated from neutral glycans and/or positively charged glycans. In some such embodiments, the negatively charged glycans comprise phosphorylated glycans, sulfated glycans, multi-acetylated sialylated glycans, or a combination thereof.

In many embodiments, separation of charged glycans is accomplished using a chromatography technique. For example, glycan preparations from which sialic acids have been released (e.g., sialidase-treated glycan preparations) can be separated using a charged column, such as in ion exchange chromatography. To separate negatively charged glycans from other glycans, for example, an anion exchange column can be used, as in anion exchange chromatography (AEC/AEX). Resins typically employed in anion exchange chromatography include, but are not limited to, Q-resin (a Quaternary amine) and DEAE resin (diethylaminoethane). Charged resins for use in anion exchange chromatography are commercially available from suppliers such as BioRad (Hercules, Calif.) and Amersham Biosciences (Chalfont St. Giles, United Kingdom).

Particular conditions for chromatography experiments may depend on the particular glycan species that are being separated, the composition of the glycan preparation, etc.

In some embodiments, one or more additional separation steps is/are performed using any method suitable for separation of molecules, including, but not limited to, methods that allow separation based on size, hydrophobicity, charge, charge-to-mass ratio, or a combination thereof, etc. Additional separation steps may be performed immediately after a previous separation step and/or after another process such as, for example, optional analyses as discussed below. As a non-limiting example, after a step of separation on an anion exchange column, a second dimension of chromatography such as normal phase amide chromatography may be used. Information from one or both steps of separation may be used to identify glycan species.

B. Analysis of Separated Glycans

In certain embodiments, provided methods comprise analyzing structural characteristics of separated and/or isolated glycans (e.g., glycans having a first charge and/or a first charge-to-mass ratio). In some embodiments, analyses may enable identifying charged glycans. Separated and/or isolated glycans may optionally be pooled from more than one glycan preparation and/or sample.

Glycans may be analyzed by any technique including, for example, ligand binding, mass spectrometry, nuclear magnetic resonance, and/or other methodologies. A variety of methods for analyzing glycans are known in the art. For example, see Anumula, Anal. Biochem., 350(1):1-23, 2006; Klein et al. Anal. Biochem.,179:162-66, 1989; and Townsend, R. R., *Carbohydrate Analysis: High Performance Liquid Chromatography and Capillary Electrophoresis*, ed. Z. El Rassi, pp. 181-209, 1995, Yuan et al., J. Chromatography A (2005) 1067:145-152, the contents of each of which are incorporated herein by reference in their entirety.

In some embodiments, analysis of glycans as described herein may comprise, for example, treating glycans to release certain saccharide (e.g., monosaccharide) components. For example, in some embodiments, glycans are treated with one or more endoglycosidase treatments.

Glycans can be analyzed by one or more of a variety of methods. As non-limiting examples, glycans can be characterized by methods such as nuclear magnetic resonance (NMR), mass spectrometry, liquid chromatography, 2-dimensional chromatography, SDS-PAGE, antibody staining, lectin staining, monosaccharide quantification, capillary electrophoresis, fluorophore-assisted carbohydrate electrophoresis (FACE), micellar electrokinetic chromatography (MEKC), exoglycosidase and/or endoglycosidase treatments, and combinations thereof. Those of ordinary skill in the art will be aware of other methods that can be used to characterize glycans.

In some embodiments, glycan structure and/or composition (e.g., monosaccharide composition) is/are analyzed by chromatographic methods, such as, for example, liquid chromatography (LC), high performance liquid chromatography (HPLC), ultra performance liquid chromatography (UPLC), thin layer chromatography (TLC), and combinations thereof.

In some embodiments, glycan structure and/or composition (e.g., monosaccharide composition) is/are analyzed by mass spectrometry (MS) and related methods, such as, for example, tandem MS, LC-MS, LC-MS/MS, matrix assisted laser desorption ionization mass spectrometry (MALDI-MS), Fourier transform mass spectrometry (FTMS), ion mobility separation with mass spectrometry (IMS-MS), electron transfer dissociation (ETD-MS), and combinations thereof.

In some embodiments, glycan structure and/or composition (e.g., monosaccharide composition) is/are analyzed by electrophoretic methods, such as, for example, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof.

In some embodiments, glycan structure and/or composition (e.g., monosaccharide composition) is/are analyzed by nuclear magnetic resonance (NMR) and related methods, including but not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In certain embodiments, glycoconjugates and/or glycan structures are labeled prior to characterization. As is known to those of ordinary skill in the art, such labeling may increase signal and/or reduce background noise during characterization. Any of a variety of labels can be used in accordance with the present disclosure, including but not limited to, fluorescent labels, radiolabels and/or chemiluminescent labels. In certain embodiments, glycan structures are labeled with fluorescent 2-aminobenzamide ("2-AB"). Those of ordinary skill in the art will be aware of other suitable labels that can be used in accordance with the present disclosure.

In some embodiments, more than one analysis technique may be employed and/or additional analyses steps are performed. Additional steps may immediately follow a previous analysis step and/or a different step (e.g., separation of glycans having a first charge and/or having a particular charge-to-mass ratio, etc.).

C. Quantification

In some embodiments, methods comprise quantifying at least one separated glycan using at least one quantification standard, that is, a known amount of a molecule that can be run in parallel to and/or along with the separated glycans. For example, in a method such as chromatography, the heights and/or areas under peak(s) representing separated glycans in a chromatogram may be extrapolated a calibration curve generated using the quantification standard(s) to obtain an approximate of the amount of separated glycans in a sample.

In some embodiments, quantification is relative, i.e., amounts of particular species of glycans are determined relative to other species. For example, the amounts of unusually modified glycan species may be determined relative to other glycan species. Alternatively or additionally, amounts of types of unusually modified glycan species (e.g., phosphorylated glycans, sulfated glycans, and/or multi-acetylated sialylated glycans) may be determined relative to each other.

In some embodiments, quantification is absolute. For example, the absolute amount of separated glycan species (such as, for example, unusually modified glycan species) is determined. Absolute quantification may be determined using, for example, a standard curve (or "calibration curve") of values obtained using quantification standards.

A standard may be "external" (that is, run separately from glycan preparations, for example, in parallel) and/or "internal" (that is, run together with glycan preparations, also known as "spiking"). Whether internal or external, the standard may be labeled. In some embodiments, glycans in the glycan preparation and the standard are both labeled. In some such embodiments, glycans and the standard are both labeled with the same type of label. Both internal and external standards may be labeled with the same type of label as the glycans. In embodiments using an internal standard with the same label, the internal standard will typically be separable and/or distinguishable from labeled glycans based on a difference such as size. For example, a standard may be much smaller in molecular weight than most glycans in a given preparation such that the standard will be expected to elute at a different timepoint than glycans in the preparation.

Molecules that may serve as suitable quantification standards include, but are not limited to, smaller versions of glycan molecules, plant carbohydrates, etc. In some embodiments, 2-aminobenzamide-chitobiose is used as a quantification standard. In some embodiments, quantification standards are obtained by cleaving glycoconjugates and/or glycans such that fragments of glycans are generated, labeling the resulting fragments, and characterizing the fragments such that their sizes as determined on relevant separation and/or analysis techniques are known.

III. Applications

It will be appreciated that the methods disclosed herein can be used in any of a variety of applications. In general, provided methods are useful in any application that involves the structural characterization of glycans (such as applications in which it is desirable to characterize glycans associated with a target glycoconjugate (e.g., a glycoprotein) and/or isolation of certain glycan species (e.g. unusually modified glycans).

Methods as described herein may be utilized, for example, to determine characteristic behavior of particular unusually modified glycans (and/or glycoconjugates containing them). Once such characteristic behavior has been determined, application of the techniques can be used to identify particular such glycans in a glycan or glycoconjugate preparation. Alternatively or additionally, techniques described herein may be used, alone or in combination with other techniques (e.g., as described herein) to isolate and/or characterize one or more glycoconjugates (e.g., containing unusually modified glycans) or glycans (e.g., unusually modified glycans). Similarly, whether or not the structure of unusually modified glycans present in detected peaks or bands is known, peak/band profiles can be compared to one another to assess differing levels/amounts of unusually modified glycans in different glycoconjugate or glycan preparations.

As mentioned previously, provided methods can be applied to glycan preparations obtained from a wide variety of sources including, but not limited to, therapeutic formulations and biological samples (e.g., samples containing cells). Such a glycan preparation may undergo one or more analysis and/or purification steps prior to or after being analyzed according to the present disclosure. For example, in some embodiments, glycans in a glycan preparation are labeled with one or more detectable markers or other agents that may facilitate analysis by techniques such as, for example, mass spectrometry or NMR. Any of a variety of separation and/or isolation steps may be applied to a glycan preparation in accordance with the present disclosure.

In some embodiments, provided methods are used to characterize and/or control or compare the quality of therapeutic products. Glycosylation can often affect the activity, bioavailability, or other characteristics of a therapeutic protein product. Provided methods can be used, for example, to assess glycosylation patterns (such as composition and/or type of unusual modifications) in cells producing a therapeutic protein product. In some embodiments, analysis is accomplished without isolating the products. Among other things, provided methods can facilitate real time analysis of glycosylation patterns in production systems for therapeutic proteins.

Provided methods may be used in one or more stages of process development for the production of a therapeutic or other commercially relevant glycoprotein of interest. Non-limiting examples of such process development stages that can employ methods of the present disclosure include cell selection, clonal selection, media optimization, culture conditions, process conditions, and/or purification procedure. Those of ordinary skill in the art will be aware of other process development stages.

Provided methods may be used to monitor the extent and/or type of glycosylation (including type(s) of unusual modifications, if any) occurring in a particular cell culture and/or under particular growth conditions, thereby allowing adjustment or possibly termination of the culture in order, for example, to achieve a particular desired glycosylation pattern or to avoid development of a particular undesired glycosylation pattern.

Provided methods can be used to assess glycosylation characteristics of cells or cell lines that are being considered for production of a particular desired glycoprotein (for example, even before the cells or cell lines have been engineered to produce the glycoprotein, or to produce the glycoprotein at a commercially relevant level).

In some embodiments, provided methods are used to monitor glycosylation pattern during culture of cells that produce a glycoprotein. For example, production of a glycoprotein (e.g., commercial production) may involve steps of (1) culturing cells that produce the glycoprotein, (2) obtaining samples at regular or irregular intervals throughout the process of culturing the cells, (3) obtaining glycan preparations from the samples, and (4) analyzing the glycosylation pattern (in particular, composition and type of unusual modifications) on glycans in the preparations. In some embodiments, the glycosylation pattern on cell surface glycoconjugates is analyzed; in some such embodiments, methods further comprise a step of comparing the cell surface glycosylation patterns of different samples to one another and/or to glycosylation patterns of one or more non-cell-surface glycoproteins produced by the relevant cell(s). In some embodiments, methods further comprise a step of comparing the glycosylation patterns for one or more obtained samples to the glycosylation pattern of a reference sample.

In some embodiments, a desired glycosylation pattern for a particular target glycoprotein is known, and the technology described herein allows monitoring of culture samples to assess progress of the production along a route known to produce the desired glycosylation pattern. For example, where the target glycoprotein is a therapeutic glycoprotein, for example having undergone regulatory review in one or more countries, it will often be desirable to monitor cultures to assess the likelihood that they will generate a product with a glycosylation pattern as close to the established glycosylation pattern of the pharmaceutical product as possible, whether or not it is being produced by exactly the same route. As used herein, "close" in reference to glycosylation pattern in comparison to that of a product refers to a glycosylation pattern having at least about a 75%, 80%, 85%, 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of unusually modified glycans.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a phosphorylated glycan.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sulfated glycan.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of an acetylated glycan.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of multi-acetylated sialylated glycans (e.g., of diacetylated glycans), or of a particular multi-acetylated glycan.

In some embodiments, a desired glycosylation pattern will have other particular features in addition to a feature related to unusual modifications. For example, in some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of core fucosylation.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sialic acid linked to an N-acctylglucosaminc.

In some embodiments, a desired glycosylation pattern (e.g., a cell surface glycosylation pattern and/or a glycosylation patterns observed with a produced non-cell-surface glycoprotein) will be more extensive. For example, in some embodiments, a desired glycosylation pattern shows high (e.g., greater than about 60%, about 65%, about 70%, about 75%, about 80%, about 85%, about 90%, about 95%, about 98%, about 99%, or more) occupancy of glycosylation sites; in some embodiments, a desired glycosylation pattern shows a high degree of branching (e.g., greater than about 60%, about 65%, about 70%, about 75%, about 80%, about 85%, about 90%, about 95%, about 98%, about 99% or more have tri or tetra-antennary structures).

In some embodiments, a desired glycosylation pattern will be less extensive. For example, in some embodiments, a desired cell surface glycosylation pattern shows low (e.g., less than about 50%, about 45%, about 40%, about 35%, about 30%, about 25%, about 20%, about 15%, about 15%, about 5%, about 1%, or less) occupancy of glycosylation sites; and/or a low degree of branching (e.g., less than about 20%, about 15%, about 10%, about 5%, about 1% or less have tri or tetra-antennary structures).

In some embodiments, a desired glycosylation pattern will be more extensive in some aspects and less extensive in others. For example, it may be desirable to employ a cell line that tends to produce glycoproteins with long, unbranched oligosaccharide chains. Alternatively, it may be desirable employ a cell line that tends to produce glycoproteins with short, highly branched oligosaccharide chains.

In some embodiments, a desired glycosylation pattern will be enriched for a particular type of glycan structure. For example, in some embodiments, a desired glycosylation pattern will have low levels (e.g., less than about 20%, about 15%, about 10%, about 5%, about 1%, or less) of high mannose or hybrid structures, high levels (e.g., greater than about 60%, about 65%, about 70%, about 75%, about 80%, about 85%, about 90%, about 95%, about 98%, about 99%, or more) of high mannose structures, high levels (e.g., greater than about 60%, about 65%, about 70%, about 75%, about 80%, about 85%, about 90%, about 95%, about 98%, about 99%, or more; for example at least one per glycoprotein) phosphorylated high mannose, or low levels (e.g., less than about 20%, about 15%, about 10%, about 5%, about 1%, or less) of phosphorylated high mannose.

In some embodiments, a desired glycosylation pattern will include at least about one sialic acid. In some embodiments, a desired glycosylation pattern will include a high level (e.g., greater than about 60%, about 65%, about 70%, about 75%, about 80%, about 85%, about 90%, about 95%, about 98%, about 99%, or more) of termini that are sialylated. In some embodiments, a desired glycosylation pattern that includes sialyation will show at least about 85%, about 90%, about 95%, about 98%, about 99%, or more N-acetylneuraminic acid and/or less than about 20%, about 15%, about 10%, about 5%, about 1%, or less N-glycolylneuraminic acid.

In some embodiments, a desired glycosylation pattern shows specificity of branch elongation (e.g., greater than about 60%, about 65%, about 70%, about 75%, about 80%, about 85%, about 90%, about 95%, about 98%, about 99%, or more of extension is on α1,6 mannose branches; or greater than about 60%, about 65%, about 70%, about 75%, about 80%, about 85%, about 90%, about 95%, about 98%, about 99%, or more of extension is on α1,3 mannose branches).

Representative therapeutic glycoprotein products whose production and/or quality can be monitored in accordance with the present disclosure include, for example, any of a variety of hematologic agents (including, for instance, erythropoietin, blood-clotting factors, etc.), interferons, colony stimulating factors, antibodies, enzymes, hormones, etc.

In some embodiments, provided are methods in which glycans from different sources or samples are compared with one another. In some such examples, multiple samples from the same source are obtained over time, so that changes in glycosylation patterns (and particularly in composition and/or type(s) of unusual modifications) are monitored. In some embodiments, glycan-containing samples are removed at regular intervals. In some embodiments, glycan-containing samples are removed at about 30-second, about 1-minute, about 2-minute, about 5-minute, about-10 minute, about-30 minute, about-1 hour, about-2 hour, about 3-hour, about 4-hour, about 5-hour, about 10-hour, about 12-hour, or about 18-hour intervals, or at even longer intervals. In some embodiments, glycan-containing samples are removed at irregular intervals. In some embodiments, glycan-containing samples are removed at 5-hour intervals.

In some embodiments, one of the samples is a historical sample, and/or a record of a historical sample is used for comparison (e.g., as in batch release testing of pharmaceutical products). In some embodiments, one of the samples is a reference sample.

In certain embodiments, changes in the glycosylation pattern of a glycoprotein of interest grown under one or more different growth parameters are tested to determine one or more desirable growth parameters, or combinations of parameters, for glycoprotein production. In some embodiments, differences in glycosylation patterns are determined by observing and/or measuring a glycosylation pattern characteristic such as, without limitation, composition and/or type(s) of unusually modified glycans, glycosylation site occupancy, identity of linked glycans, relative amounts of linked glycans, complete or partial composition of linked glycans, and/or relative amounts of linked glycans. Alternatively or additionally, other glycosylation pattern characteristics known to those of ordinary skill in the art may be measured.

In some embodiments, methods provided herein are used to monitor the extent and/or type of glycan modifications occurring in different samples (e.g., in different cell cultures).

In some embodiments, glycans from different cell culture samples prepared under conditions that differ in one or more selected parameters (e.g., cell type, culture type [e.g., continuous feed vs batch feed, etc.], culture conditions [e.g., type of media, presence or concentration of particular component of particular medium(a), osmolarity, pH, temperature, timing or degree of shift in one or more components such as osmolarity, pH, temperature, etc.), culture time, isolation steps, etc.) but are otherwise identical, are compared, so that effects of the selected parameter(s) on glycan modifications and/or other characteristics of glycosylation patterns are determined. In certain embodiments, glycans from different cell culture samples prepared under conditions that differ in a single selected parameter are compared so that effect of the single selected parameter on glycan modifications and/or other characteristics of glycosylation patterns is determined. Among other applications, therefore, the present techniques may facilitate determination of the effects of particular parameters on glycosylation patterns in cells.

In some embodiments, glycans from different batches of cells that produce a glycoprotein of interest (e.g., a therapeutic glycoprotein), whether prepared by the same method or by different methods, and whether prepared simultaneously or separately, are compared. In such embodiments, the present disclosure facilitates quality control of glycoprotein preparation (i.e., of preparation of a target glycoprotein preparation). In some embodiments, methods facilitate monitoring of progress of a particular culture producing a glycoprotein of interest (e.g., when samples are removed from the culture at different time points and are analyzed and compared to one another). In any of these embodiments, features of the glycan analysis can be recorded, for example in a quality control record. As indicated above, in some embodiments, a comparison is made with a historical record of a prior or standard batch of glycoprotein, and/or with a reference sample.

In certain embodiments, the present disclosure may be used in studies to modify the glycosylation characteristics of a cell, for example to establish a cell line and/or culture conditions with one or more desirable unusual modifications. Such a cell line and/or culture conditions can then be used, if desired, for production of a particular target glycoconjugate (e.g., glycoprotein) for which such glycosylation characteristic(s) is/are expected to be beneficial.

According to the present disclosure, techniques described herein can be used to detect desirable or undesirable glycans, for example to detect or quantify the presence of one or more contaminants in a product, or to detect or quantify the presence of one or more active or desired species.

In various embodiments the methods can be used to assess glycosylation of one or more biomarkers indicative of, e.g., a disease state, prior to the appearance of symptoms and/or progression of the disease state to an untreatable or less treatable condition, by detecting one or more specific glycans whose presence or level (whether absolute or relative) may be correlated with a particular disease state (including susceptibility to a particular disease) and/or the change in the concentration of such glycans over time. For example, in some embodiments of the disclosure, the target glycoconjugate is a biomarker.

In certain embodiments, provided methods are used to isolate particular glycans, e.g., a particular glycan species or set of glycan species. For example, provided methods may be used to isolate unusually modified glycans such as, e.g., phosphorylated glycans, sulfated glycans, multi-acetylated sialylated glycans, or a combination thereof.

In certain embodiments, methods described herein facilitate detection and/or isolation of particular glycans (e.g., unusually modified glycans) that are present at very low levels in a source (e.g., a biological sample). In such embodiments, it is possible to detect and/or optionally quantify the levels of glycans that are present at levels less than about 10%, 5%, 4%, 3%, 2%, 1.5%, 1%, 0.75%, 0.5%, 0.25%, 0.1%, 0.075%, 0.05%, 0.025%, or 0.01% within a population of glycans in a source. In some embodiments, it is possible to detect and/or optionally quantify the levels of glycans comprising between 0.1% and 5%, e.g., between 0.1% and 2%, e.g., between 0.1% and 1% of a glycan preparation. In certain embodiments, it is possible to detect and/or optionally quantify the levels of glycans at between about 0.1 fmol to about 1 mmol.

In some embodiments, techniques described herein may be combined with one or more other technologies for the detection, analysis, and or isolation of glycans or glycoconjugates.

IV. Databases

In some embodiments, separated glycans are compared to previously identified separated glycans. Such comparisons may enable analysis of separated glycans. In some embodiments, characteristics of previously identified glycans are stored in a database. Analysis of separated glycans may, for example, comprise using information in a database.

Provided methods can also comprise generating a list of glycan properties such as, for example, behavior of particular unusually modified glycans when exposed to one or more different analytic techniques. Also provided are methods of generating a list of properties of particular glycans and/or glycoconjugate preparations. Representative such properties include, for example, presence or amount of a particular unusually modified glycan in the preparation, degree of occupancy of one or more particular glycosylation sites, (e.g., with unusually modified glycans), types of glycans (e.g., unusually modified glycans present), relative amounts of different glycans (e.g., unusually modified glycans), etc. In some embodiments, a list comprises the number of one or more types of monosaccharides present in a glycan or glycoconjugate preparation. The list can also or alternatively include the total mass of the glycan or glycoconjugate, the mass of the non-saccharide moiety of a glycoconjugate, the mass of one and/or more unusually modified glycans, etc One example of such a method includes measuring 1, 2, 3, 4, 5, 6, 7, 8, 9, 10 or more properties of a particular glycan, glycan preparation, or glycoconjugate preparation, and recording a value for the one or more properties to generate a list of the glycan properties. Such methods may also or alternatively comprise generating a list of glycoconjugate properties.

In some embodiments, the list is a data structure tangibly embodied in a computer-readable medium, such as computer hard drive, floppy disk, CD-ROM, etc. For example, a data structure can have a plurality of entries, wherein each entry encodes a value of a property. The entries can be encoded by any kind of value, for example, as single-bit values, single-digit hexadecimal values, decimal values, etc.

Also provided are databases, tangibly embodied in one or more computer-readable media, wherein the databases stores information descriptive of one or more glycans, glycan preparations and/or glycoconjugate preparations (such as information on composition and/or type of unusual modifications). Provided databases comprise data units that correspond to the glycan and/or glycoconjugate. Data units include an identifier that includes one or more fields, each field storing a value corresponding to one or more properties of the glycans and/or glycoconjugates. In some embodiments, the identifier includes 2, 3, 4, 5, 6, 7, 8, 9, 10 or more fields. A database, for example, can be a database of all possible glycoconjugates and/or glycans or can be a database of values representing a glycome profile or pattern for one or more samples.

Provided are improved methods for analyzing samples containing glycans (e.g., unusually modified glycans), wherein a combined analytical-computational platform is used to achieve a thorough characterization of glycans. Any of the methods described herein can be combined with computational methods. Diverse information gathered from the different experimental techniques can be used to generate constraints. Generation of constraints can be done in combination with a panel of proteomics and glycomics-based bioinformatics tools and databases for the efficient characterization (unusual modifications, glycosylation site occupancy, quantification, glycan structure, etc.) of the glycan/glycoconjugate mixture of interest. Databases can be those known in the art or can be generated with provided methods. As an example, a method of analyzing glycans with the combined analytic and computational techniques can include performing an experiment on a sample containing glycans, analyzing the results of the experiment, generating constraints, and solving them. The constraints can be generated and/or solved with the data obtained from experimental results as well as other known information, such as information from databases that contain information about glycans or glycoconjugates and with other tools that analyze the properties of glycans, glycoconjugates or the non-saccharide moieties thereof, such as mass and enzyme action.

Constraints can be generated using, for instance, what is known of the biosynthetic pathway of glycan synthesis.

V. Kits

Reagents useful for the practice of one or more provided methods may desirably be provided together, assembled in a kit. In certain embodiments, kits of the present disclosure include one or more reagents useful for releasing glycoproteins from cells (e.g., one or more proteases, glycosidases, and/or other agents), one or more sialidases, and/or supplementary components such as buffers, co-factors, etc. In certain embodiments, kits of the present disclosure include one or more reagents useful for purifying and/or analyzing the glycan preparations.

In some embodiments, provided kits include one or more reagents useful for cleaving glycan structures from a glycoprotein or glycopeptide (e.g., enzymes such as PNGase F, PNGase A, O-glycanase and/or Endo-H). In some embodiments, kits of the present disclosure include one or more reagents useful for purifying the cleaved glycan structures from the protein component of glycoproteins or glycopeptides (e.g., one or more glycosidases).

In some embodiments, kits include one or more reagents for labeling glycan structures. For example, kits of the present disclosure may include fluorescent labels, radiolabels and/or chemiluminescent labels. In certain embodiments, kits of the present disclosure include fluorescent 2-aminobenzamide ("2-AB").

In certain embodiments, provided kits include one or more reagents for culturing cells (e.g., cell culture media, buffers, media components, etc.) and/or purifying cells after the cells have been cultured.

EXEMPLIFICATION

Example 1

Identification and Quantification of Unusually Modified Glycan Species

Presented in this example are experimental results using a provided method for identifying and quantifying unusually modified glycan species.

Glycans are first released from a glycoprotein of interest by enzymatic or chemical methods (for example, using PNGase F, hydrazinolysis, etc.). Released glycans are then labeled using a 2-aminobenzamide fluorescent label. A sample of fluorescently-labeled N-glycan mixture is then treated with a sialidase enzyme and incubated overnight at 37° C. Following incubation, the sample is injected on an anion-exchange column and the retained species (which comprises negatively charged species) are collected and analyzed by mass spectrometry.

Separately, a calibration curve is generated using an external standard containing the same fluorescent label as the labels of the glycans in the mixture. The unusually modified glycans are then quantified by extrapolating their peak height/area to the calibration curve. Alternatively, the unusually modified glycans (e.g., phosphorylated glycans, sulfated glycans, and/or multi-acetylated sialylated glycans) can be analyzed on a second dimension of chromatography (such as normal phase amide) and identity of the species can be determined from retention times in both chromatographic separations in comparison to predetermined glycan species.

Figure 3:
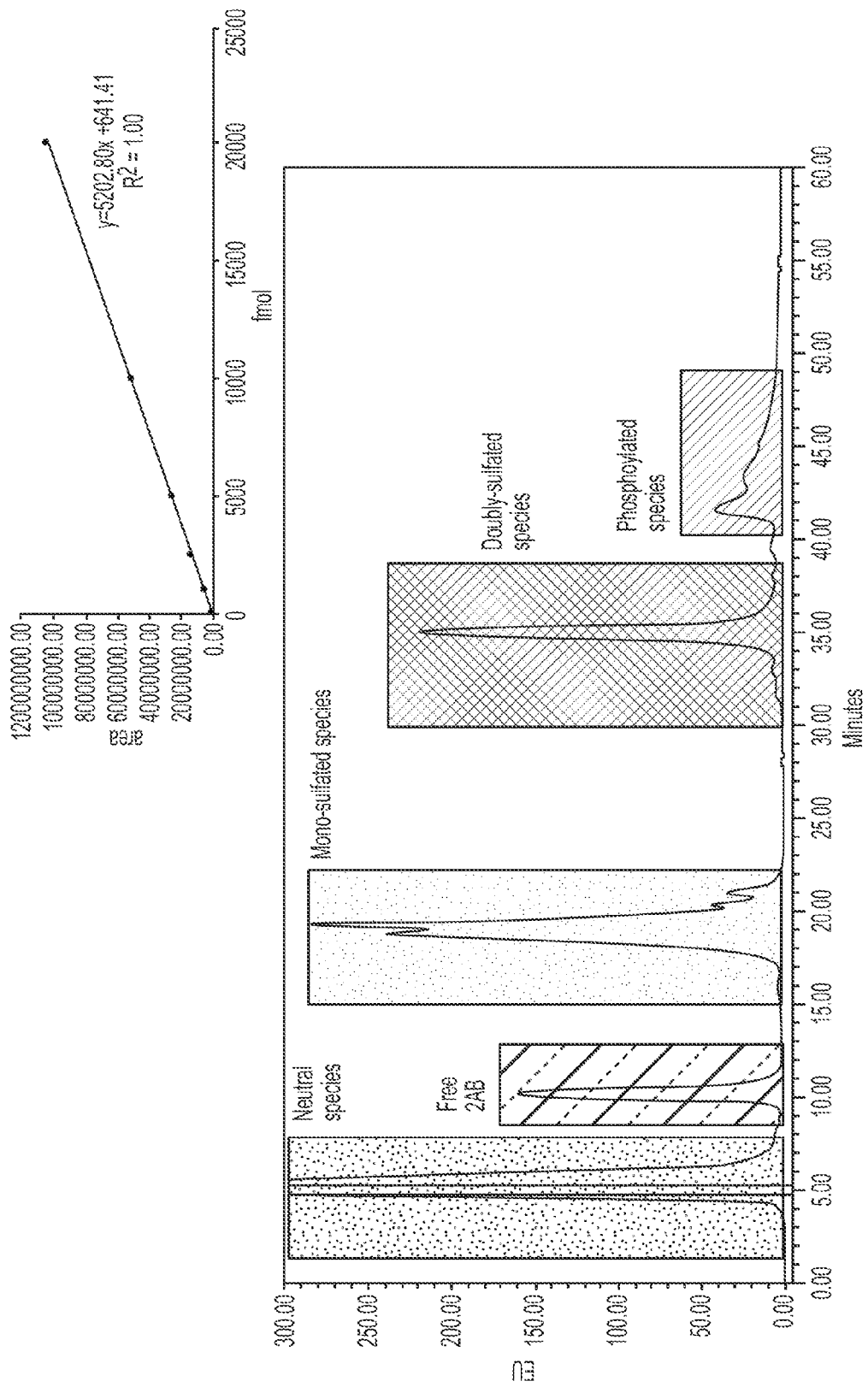
FIG. 3 depicts an anion exchange chromatography-high performance liquid chromatography (AEX-HPLC) profile of unusually modified species derived from an erythropoietin therapeutic glycoprotein with biological activity, obtained from a Chinese research source, after sialidase treatment. The insert depicts a calibration curve using 2-aminobenzamide-chitobiose as an external standard. The peaks identified here as an unusually modified species was further identified as phosphorylated N-glycans and sulfated glycans.
Figure 4:
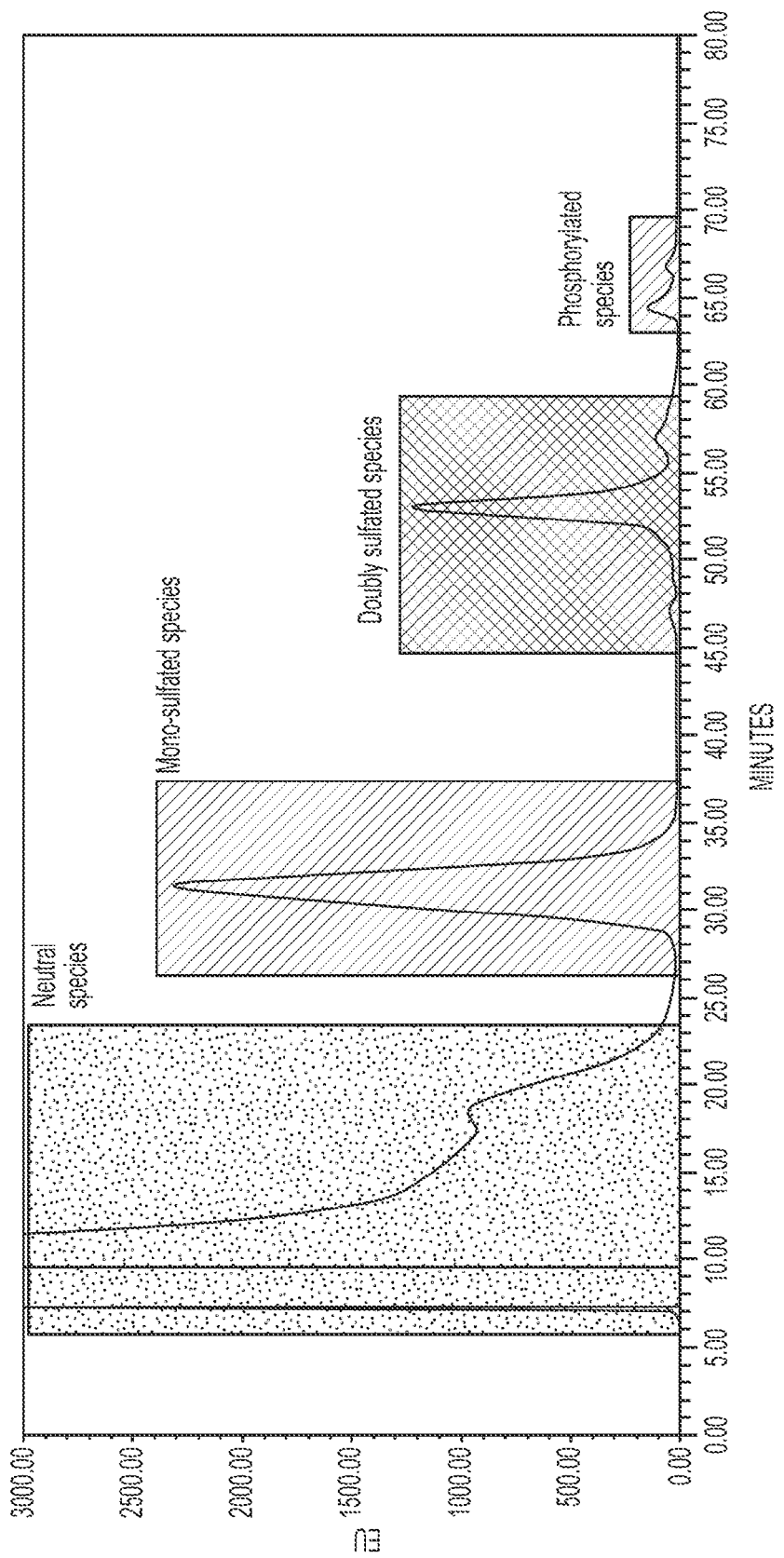
FIG. 4 depicts an anion exchange chromatography-high performance liquid chromatography (AEX-HPLC) profile of unusually modified species derived from a second glycoprotein of interest with biological activity, with 97% amino acid sequence identity to the erythropoietin therapeutic glycoprotein described in FIG. 3, after sialidase treatment. The peaks identified here as an unusually modified species was further identified as phosphorylated N-glycans and sulfated glycans.

As shown in FIGS. 3 and 4, unusually modified glycans elute later than neutral (desialyated) glycans. This protocol can therefore be applied to glycan mixtures to separate unusually modified species from other glycans in the mixture. Quantities of unusually modified glycans can be determined using the calibration curve shown in the inset of FIG. 3. Similar results were obtained from quantitation analysis of unusually modified glycans identified in FIG. 4 (data not shown).

As described herein, FIG. 3 depicts an AEX-HPLC profile of unusually modified glycan species derived from an erythropoietin therapeutic glycoprotein with biological activity obtained from a Chinese research source. FIG. 4 depicts an AEX-HPLC profile of unusually modified glycan species derived from a second therapeutic glycoprotein of interest with 97% amino acid identity to the erythropoietin glycoprotein described in FIG. 3. The profile of the unusually modified glycans from each therapeutic glycoprotein sample are different from one another. These data confirm that the provided methods distinguish between highly similar glycoprotein preparations (e.g., in terms of glycan components). Similar data have been obtained for antibody glycoprotein preparations as well (see FIGS. 5-7).

Figure 5:
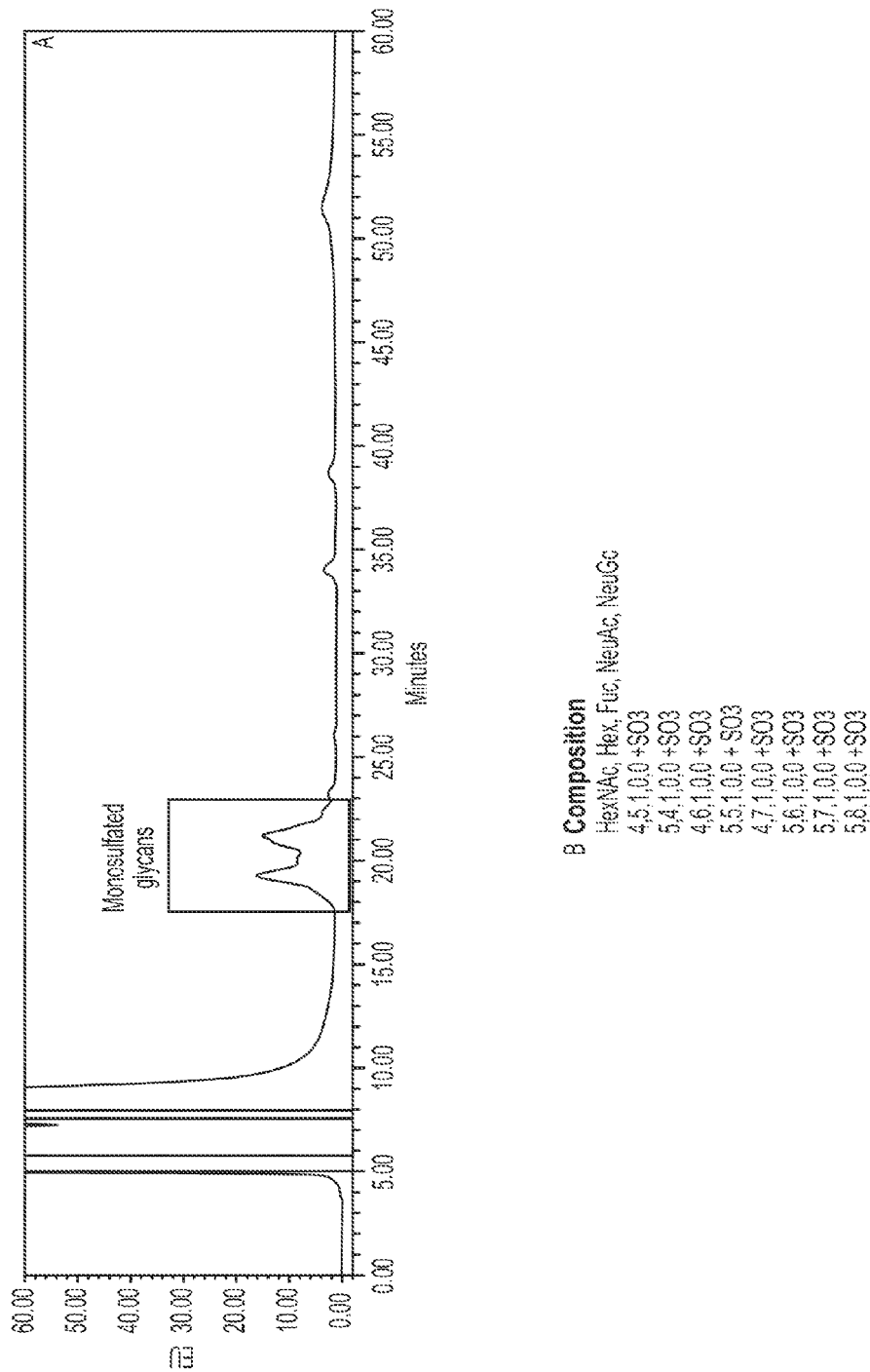
FIG. 5 depicts results from a chromatographic analysis of sulfated glycans derived from monoclonal anti-EGFR antibody produced in mouse. Composition of glycans within the peak were identified by mass spectrometry. In the nomenclature used in panel B, "5,4,1,0,0+SO3" corresponds to HexNAc5, Hex4, Fuc1, NeuAc0, NeuGc0+one sulfate, for example.
Figure 6:
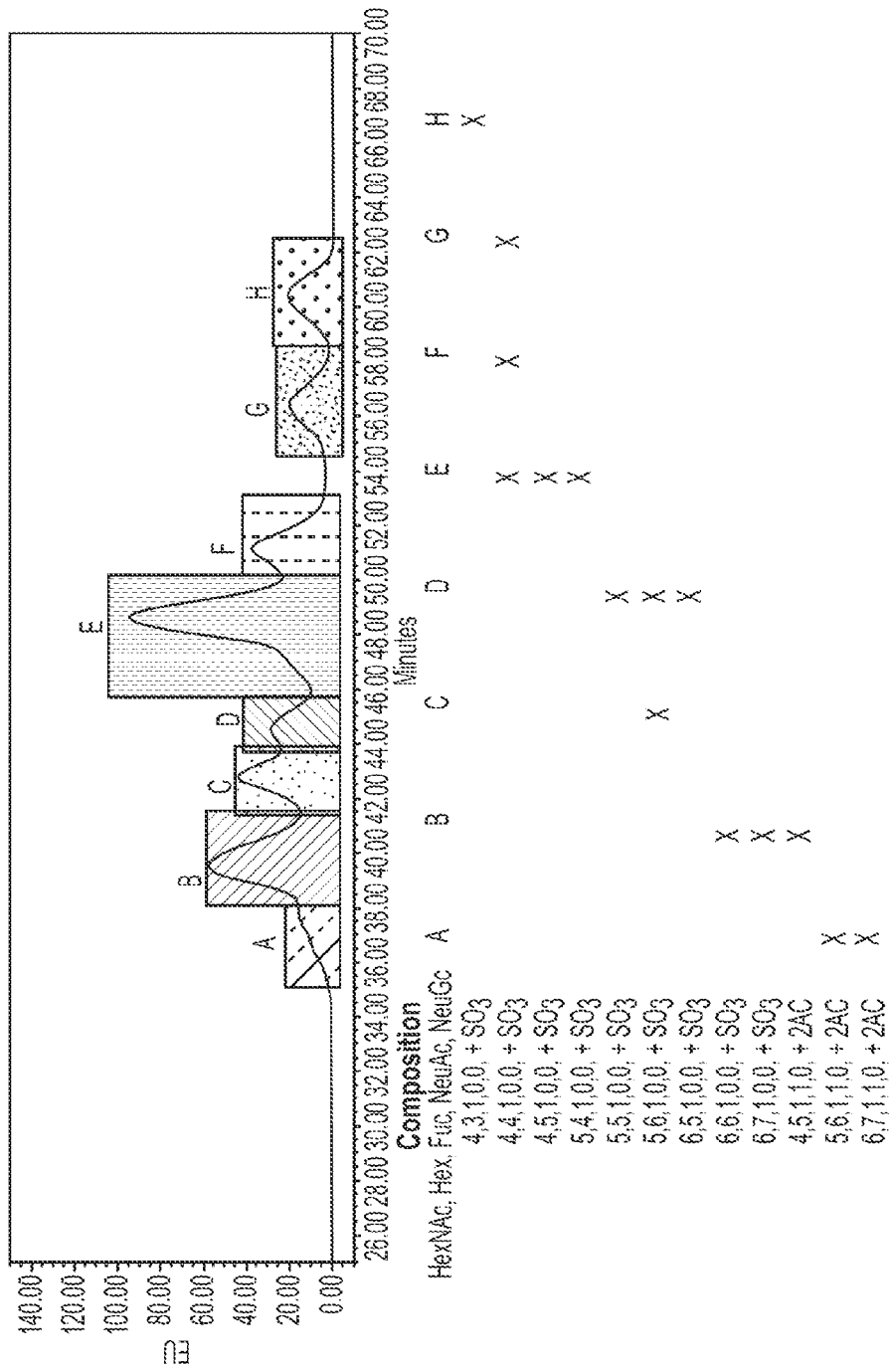
FIG. 6 depicts results from a chromatographic analysis of sulfated and diacetylated sialylated glycans derived from CTLA4-IgG from a single clone (clone 1). Composition of glycans within the peak were identified by mass spectrometry.
Figure 7:
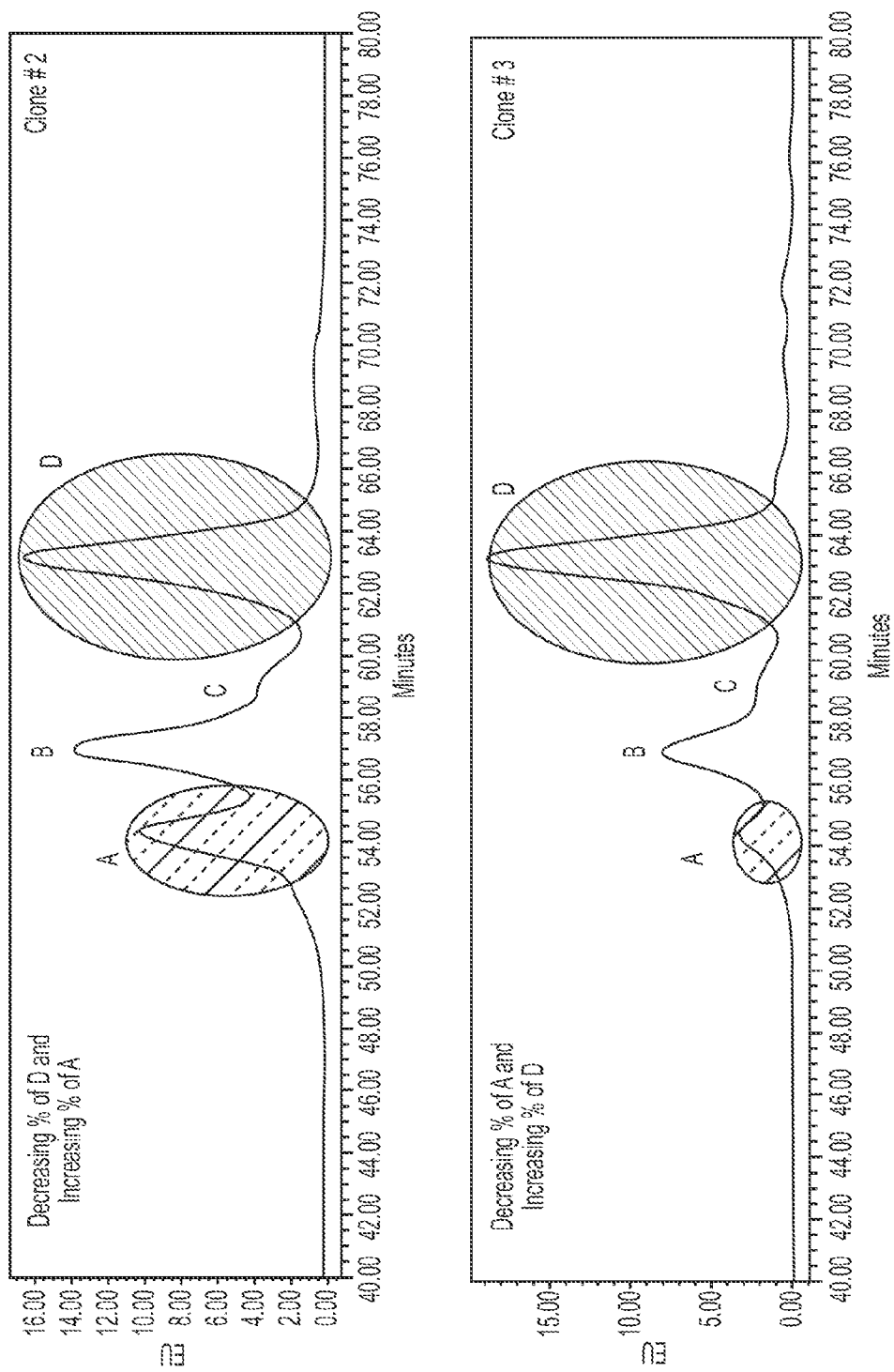
FIG. 7 depicts results from a chromatographic analysis of sulfated and diacetylated sialylated glycans derived from CTLA4-IgG from two different single clones (clone 2, top panel; clone 3, bottom panel).

As shown in FIGS. 5, 6 and 7, high resolution chromatography allows for separation of species with the same charge state, such as monosulfated glycans, and are quantifiable under the stated separation conditions. FIG. 5 depicts chromatographic analysis of sulfated glycans derived from a monoclonal anti-EGFR antibody produced in mouse. FIGS. 6 and 7 depict chromatographic analysis of unusually modified glycans derived from individual clones of anti-CTLA4-IgG monoclonal antibody. These data confirm that provided methods distinguish between glycoproteins produced by different cell lines (e.g., different clones).

Equivalents

Those skilled in the art will recognize, or be able to ascertain using no more than routine experimentation, many equivalents to the specific embodiments of the disclosure, described herein. Other embodiments will be apparent to those skilled in the art from a consideration of the specification or practice of the invention disclosed herein. It is intended that the specification and examples be considered as exemplary only, with the true scope of the invention being indicated by the following claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of, the group members are present in, employed in, or otherwise relevant to a given product or process.

Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein arc included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the disclosure, or aspects of the disclosure, is/are referred to as comprising particular elements, features, etc., certain embodiments of the disclosure or aspects of the disclosure consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any exoglycosidase, any glycosidic linkage, any reaction condition, any method of purification, any method of product analysis, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

What is claimed is:

1. A method comprising steps of:
   a) providing a glycan preparation comprising multi-acetylated sialylated glycans, wherein the glycan preparation is obtained by releasing glycans from a glycoconjugate;
   b) releasing sialic acids by exposing the glycan preparation to at least one agent that cleaves sialic acid residues;
   c) separating glycans in the agent-treated glycan preparation based on charge to mass ratio; and
   d) quantifying at least one separated multi-acetylated sialylated glycan using at least one quantification standard.

2. The method of claim 1, wherein the multi-acetylated sialylated glycans comprise less than about 50% of the glycans present in the glycan preparation.

3. The method of claim 2, wherein the multi-acetylated sialylated glycans comprise less than about 10% of the glycans present in the glycan preparation.

4. The method of claim 2, wherein the multi-acetylated sialylated glycans comprise less than about 5% of the glycans present in the glycan preparation.

5. The method of claim 2, wherein the multi-acetylated sialylated glycans comprise less than about 1% of the glycans present in the glycan preparation.

6. The method of claim 2, wherein the multi-acetylated sialylated glycans comprise less than about 0.1% of the glycans present in the glycan preparation.

7. The method of claim 2, wherein the multi-acetylated sialylated glycans comprise less than about 0.05% of the glycans present in the glycan preparation.

8. The method of claim 1 further comprising analyzing structural characteristics of separated glycans.

9. The method of claim 1, further comprising analyzing the monosaccharide composition of separated glycans.

10. The method of claim 8 or 9, wherein the step of analyzing comprises performing a technique selected from the group consisting of nuclear magnetic resonance (NMR), mass spectrometry, liquid chromatography, two-dimensional chromatography, capillary electrophoresis (CE), and combinations thereof.

11. The method of claim 1, 8, or 9, further comprising comparing separated glycans to previously identified separated glycans.

12. The method of claim 11, wherein characteristics of the previously identified separated glycans are stored in a database.

13. The method of claim 10, further comprising comparing separated glycans to previously identified separated glycans.

14. The method of claim 13, wherein characteristics of the previously identified separated glycans are stored in a database.

15. The method of claim 10, further comprising repeating the step of analyzing at least once.

16. The method of claim 1, wherein the glycans are separated on a charged column.

17. The method of claim 16, wherein the charged column is an anion exchange column.

18. The method of claim 1, further comprising a step of labeling glycans in the glycan preparation.

19. The method of claim 18, wherein the quantification standard is labeled with the same labels as the glycans.

20. The method of claim 1, wherein the glycoconjugate comprises a glycoprotein.

21. The method of claim 1, wherein the glycans are released using a glycosidase polypeptide.

22. The method of claim 1, wherein the glycoconjugate is obtained from a therapeutic formulation, a commercial biological product, a bioreactor, or a biological sample.

23. The method of claim 1, wherein the glycoconjugate is obtained from a tissue culture, a human or animal tissue, a plant, a fruit, a vegetable, or a combination thereof.

24. The method of claim 22, wherein the glycoconjugate is obtained from a bodily fluid.

25. The method of claim 24, wherein the bodily fluid is serum, plasma, blood, saliva, seminal fluid, urine, cerebrospinal fluid, or a combination thereof.

26. The method of claim 1, further comprising identifying at least one of the separated glycans.

27. The method of claim 1, further comprising performing one or more techniques that allows separation of molecules based on size, hydrophobicity, charge, or a combination thereof.

28. The method of claim 1, further comprising recording the result of the quantification step in a quality control record for the glycoconjugate.

29. The method of claim 28, wherein the glycoconjugate is a therapeutic glycoconjugate.

30. The method of claim 29, further comprising comparing the result of the quantification step with a reference sample of the glycoconjugate.

31. The method of claim 1, wherein the glycoconjugate is obtained from a cell that expresses the glycoconjugate.

32. The method of claim 31, further comprising comparing the result of the quantification step with a reference sample of the glycoconjugate.

33. The method of claim 32, further comprising assessing the likelihood that the cell will generate the glycoconjugate with a glycosylation characteristic close to the established glycosylation characteristic of the reference sample based on the comparison.

* * * * *

UNITED STATES PATENT AND TRADEMARK OFFICE
CERTIFICATE OF CORRECTION

| | | |
|---|---|---|
| PATENT NO. | : 9,103,821 B2 | Page 1 of 1 |
| APPLICATION NO. | : 13/140553 | |
| DATED | : August 11, 2015 | |
| INVENTOR(S) | : Bosques et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this
Third Day of May, 2016

Michelle K. Lee
*Director of the United States Patent and Trademark Office*

UNITED STATES PATENT AND TRADEMARK OFFICE
CERTIFICATE OF CORRECTION

PATENT NO. : 9,103,821 B2
APPLICATION NO. : 13/140553
DATED : August 11, 2015
INVENTOR(S) : Carlos J. Bosques et al.

Page 1 of 1

It is certified that error appears in the above-identified patent and that said Letters Patent is hereby corrected as shown below:

On title page, under item "(75) Inventors:", line 3, delete "Sibel Nur Gunay" and insert
--Nur Sibel Gunay-- therefore.

Signed and Sealed this
Tenth Day of May, 2016

Michelle K. Lee
*Director of the United States Patent and Trademark Office*